(12) United States Patent
Yamada et al.

(10) Patent No.: US 6,482,948 B1
(45) Date of Patent: Nov. 19, 2002

(54) THIENOPYRIMIDINE COMPOUNDS AND SALTS THEREOF AND PROCESS FOR THE PREPARATION OF THE SAME

(75) Inventors: Hirokazu Yamada, Niigata (JP); Nobuhiro Umeda, Kanagawa (JP); Seiichi Uchida, Kanagawa (JP); Yasuyuki Shiinoki, Kanagawa (JP); Hiromi Horikoshi, Hokkaido (JP); Nobuo Mochizuki, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/914,825

(22) PCT Filed: Mar. 29, 2000

(86) PCT No.: PCT/JP00/01957

§ 371 (c)(1),
(2), (4) Date: Aug. 31, 2001

(87) PCT Pub. No.: WO00/59912

PCT Pub. Date: Oct. 12, 2000

(30) Foreign Application Priority Data

Mar. 30, 1999 (JP) ............................................. 11-087547
Apr. 9, 1999 (JP) ............................................. 11-102287

(51) Int. Cl.[7] ............................................. C07D 409/14
(52) U.S. Cl. ..................................... 544/250; 544/115
(58) Field of Search ............................... 544/250, 251, 544/115; 541/250, 115

(56) References Cited

FOREIGN PATENT DOCUMENTS

| EP | 0 728 759 A1 | 8/1996 |
|---|---|---|
| WO | WO98/06722 | 8/1996 |
| WO | WO98/17668 | 10/1996 |
| WO | WO99/28325 | 11/1997 |

Primary Examiner—John M. Ford
(74) Attorney, Agent, or Firm—Dennis G. LaPointe; Mason & Associates, PA

(57) ABSTRACT

Thieno[2,3-d]pyrimidine compounds of general formula (1)

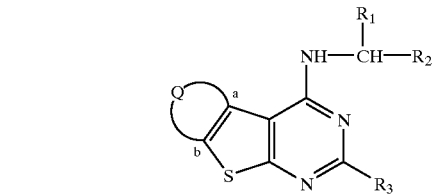

useful as drugs having a cGMP-specific phosphodiesterase inhibiting effect and the preparation thereof wherein Q is formula: $(CH_2)_n$—$N(r_1)$—$C(r_2)$ $(r_3)$, CH=CH—CH=CH, or $(CH_2)_m$ which is bonded to a and b; $R_1$ is hydrogen or $C_1$–$C_6$ alkyl; $R_2$ is $C_3$–$C_8$ cycloalkyl optionally substituted with $G_1$, phenyl optionally substituted with $G_2$, or a saturated or unsaturated heterocyclic group having 1 to 4 heteroatoms selected from N, O and S and being optionally substituted with $G_3$; and $R_3$ is a saturated or unsaturated heretocyclic group having 1 to 4 heteroatoms selected from N, O and S and being optionally substituted with $G_3$ or $(CH_2)_kC(=O)R_4$ or CH=CHC(O)$R_4$.

2 Claims, No Drawings

THIENOPYRIMIDINE COMPOUNDS AND SALTS THEREOF AND PROCESS FOR THE PREPARATION OF THE SAME

The present invention relates to pyridothienopyrimidine compounds useful as selective cGMP phosphodiesterase (PDE) inhibitors and salts thereof, and processes for the preparation of the same.

BACKGROUND ART cGMP is a substance playing an important role as a second messenger in the signal transduction system in vivo. Inhibitors of selective cGMP phosphodiesterase (PDE), which is a hydrolase of cGMP, raise cGMP levels in cells and are useful for the prevention and/or therapy of, for example, hypertension, heart failure, cardiac infarction, angina pectoris, arteriosclerosis, restenosis after PTCA (percutaneous transluminal coronary angioplasty), cardiac edema, pulmonary hypertension, renal failure, renal edema, hepatic edema, asthma, bronchitis, dementia, immunodeficiency, glaucoma or impotentia.

Compounds represented by the following formula are reported as cGMP PDE inhibitors having thieno[2,3-d] pyrimidine skeletons in WO 98/06722 and EP 728759.

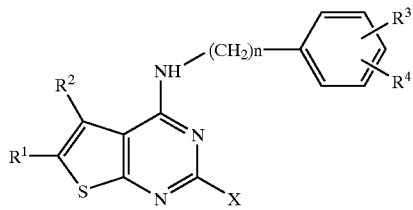

wherein, X is an optionally substituted cycloalkyl, phenyl or heterocyclic ring.

Furthermore, WO 98/17668, WO 99/28325 and WO 99/55708 have disclosed compounds represented by the following formulae.

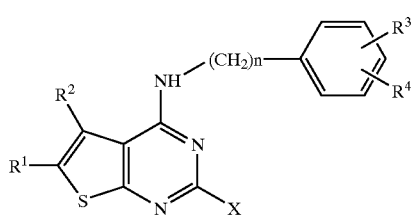

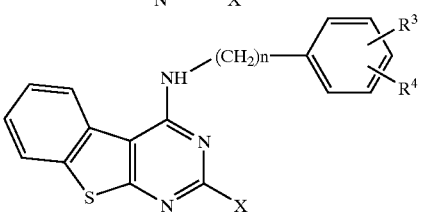

wherein, X is a group, such as alkylene or cycloalkyl, substituted with carboxylic acid, carboxylic acid amide or the like.

DISCLOSURE OF THE INVENTION

The present invention is directed to (a) a thienopyrimidine compound represented by Formula (1)

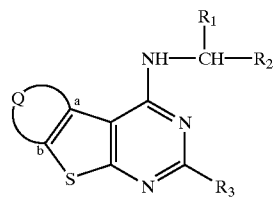

(1)

[wherein, Q is a group bound from a to b and represented by Formula $(CH_2)n—N(r_1)—C(r_2)$ $(r_3)$, $CH=CH—CH=CH$ or $(CH_2)m$;

$r_1$ is hydrogen, $C_{1-6}$ alkyl, $C_{1-6}$ alkylsulfonyl, benzyl optionally substituted with $G_1$, or a group represented by Formula $C(=O)r_4$ or $C(=O)Or_5$;

$r_2$ and $r_3$ are, each independently, hydrogen, $C_{1-6}$ alkyl or phenyl optionally substituted with $G_1$, or $r_2$ and $r_3$ join together to form oxo;

$r_4$ is hydrogen, $C_{1-6}$ alkyl, $C_{2-6}$ alkenyl, phenyl optionally substituted with $G_1$, or a saturated or unsaturated heterocyclic group containing 1 to 4 N, O or S atoms and optionally substituted with $G_3$;

$r_5$ is hydrogen, $C_{1-6}$ alkyl, $C_{2-6}$ alkenyl or optionally substituted phenyl;

n is 1, 2 or 3; m is 3, 4 or 5;

$R_1$ is hydrogen or $C_{1-6}$ alkyl;

$R_2$ is $C_{3-8}$ cycloalkyl optionally substituted with $G_1$, phenyl optionally substituted with $G_2$, or a saturated or unsaturated heterocyclic group containing 1 to 4 N, O or S atoms and optionally substituted with $G_3$;

$R_3$ is a saturated or unsaturated heterocyclic group containing 1 to 4 N, O or S atoms and optionally substituted with $G_3$, or a group represented by Formula $(CH_2)_kC(=O)R_4$ or $CH=CHC(O)R_4$;

$R_4$ is hydrogen, hydroxy, $C_{1-6}$ alkoxy, phenoxy optionally substituted with $G_2$, benzyloxy optionally substituted with $G_2$, or a group represented by Formula $Nr_6r_7$ or $NHNr_8r_9$;

$r_6$ and re are hydrogen or $C_{1-6}$ alkyl;

$r_7$ and $r_9$ are hydrogen, $C_{3-8}$ cycloalkyl, $C_{1-6}$ alkyl optionally substituted with a saturated or unsaturated heterocyclic group containing 1 to 4 N, O or S atoms which may be substituted with $C_{1-6}$ alkoxycarbonyl or $G_3$, phenyl optionally substituted with $G_1$, benzyl optionally substituted with $G_1$, or a saturated or unsaturated heterocyclic group containing 1 to 4 N, O or S atoms and optionally substituted with $G_3$;

$r_6$ and $r_7$ may join, together with N, to form a ring

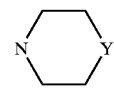

(wherein, Y is O, $CH_2$ or $Nr_{10}$);

$r_{10}$ is hydrogen, $C_{1-6}$ alkyl, phenyl optionally substituted with $G_1$, or benzyl optionally substituted with $G_1$;

k is 0, 1 or 2;

$G_1$ is halogen, $C_{1-6}$ alkyl or $C_{1-6}$ alkoxy;

$G_2$ is halogen, $C_{1-6}$ alkyl, $C_{1-6}$ alkoxy or $C_{1-2}$ alkylenedioxy;

$G_3$ is halogen, $C_{1-6}$ alkyl, $C_{1-6}$ haloalkyl, $C_{1-6}$ alkoxy or $C_{1-6}$ alkoxycarbonyl;

Substituents $G_1$, $G_2$ and $G_3$ on the benzene ring, cycloalkyl or heterocyclic ring may have two or more substituents which may be the same or different;

when $R_3$ is a saturated or unsaturated heterocyclic group containing 1 to 4 N, O or S atoms and optionally substituted with $G_3$, Q is $(CH_2)n$—$N(r^1)$—$C(r^2)$ $(r^3)$ ($r^1$, $r^2$, $r^3$ and n are as defined above), and when Q is $(CH_2)m$ or CH=CH—CH=CH, $R_4$ is anilino or k=0), and pharmaceutically acceptable salts thereof.

In more detail, the present invention is directed to:

2. a compound represented by Formula (1-1)

(1-1)

(wherein, $R_1$, $R_2$, $R_3$, $r_1$, $r_2$ and $r_3$ are as defined above); and 3. a compound represented by Formula (1-2)

(1-2)

(wherein, Q' is a group bound from a to b and represented by Formula CH=CH—CH=CH or $(CH_2)m$, and $R_1$, $R_2$, $R_4$ and m are as defined above); and furthermore 4. a process for the preparation of a compound of the said Formula (1), characterized by a reaction of a compound of Formula (3)

(3)

(wherein, Q and $R_3$ are as defined above and X is halogen), with a compound of Formula (4)

$$H_2N\text{---}\underset{\underset{R_1}{|}}{CH}\text{---}R_2$$
(4)

(wherein, $R_1$ and $R_2$ are as defined above).

Forms to Implement the Invention:

In the compounds of the present invention, represented by the said Formula (1)

$r_1$ is hydrogen; $C_{1-6}$ alkyl such as methyl, ethyl, propyl, isopropyl, butyl, isobutyl, s-butyl or t-butyl; $C_{1-6}$ alkylsulfonyl such as methylsulfonyl, ethylsulfonyl, propylsulfonyl, isopropylsulfonyl, butylsulfonyl or t-butylsulfonyl; benzyl (optionally substituted at arbitrary positions with halogen such as fluorine, chlorine or bromine; $C_{1-6}$ alkyl such as methyl or ethyl; or $C_{1-6}$ alkoxy such as methoxy or ethoxy); or a group represented by Formula C(=O)$r_4$ or C(=O)O$r_5$.

$r_2$ and $r_3$ are, each independently, hydrogen; $C_{1-6}$ alkyl such as methyl, ethyl, propyl, isopropyl, butyl, isobutyl, s-butyl or t-butyl; or phenyl (optionally substituted at arbitrary positions with halogen such as fluorine, chlorine or bromine; $C_{1-6}$ alkyl such as methyl or ethyl; or $C_{1-6}$ alkoxy such as methoxy or ethoxy), or $r^2$ and $r^3$ join together to form oxo;

$r_4$ is hydrogen; $C_{1-6}$ alkyl such as methyl, ethyl, propyl, isopropyl, butyl, isobutyl, s-butyl or t-butyl; $C_{2-6}$ alkenyl such as ethenyl, 1-propenyl or 2-propenyl; phenyl (optionally substituted at arbitrary positions with halogen such as fluorine, chlorine or bromine; $C_{1-6}$ alkyl such as methyl or ethyl; or $C_{1-6}$ alkoxy such as methoxy or ethoxy); or a saturated or unsaturated heterocyclic group containing 1 to 4 N, O or S atoms (optionally substituted at arbitrary positions with halogen such as fluorine, chlorine or bromine; $C_{1-6}$ alkyl such as methyl or ethyl; $C_{1-6}$ haloalkyl such as chloromethyl, dichloromethyl, trichloromethyl, fluoromethyl, difluoromethyl or trifluoromethyl; $C_{1-6}$ alkoxy such as methoxy or ethoxy; or $C_{1-6}$ alkoxycarbonyl such as methoxycarbonyl or ethoxycarbonyl), such as furyl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl.

$r_5$ is hydrogen; $C_{1-6}$ alkyl such as methyl, ethyl, propyl, isopropyl, butyl, isobutyl, s-butyl or t-butyl; $C_{2-6}$ alkenyl such as ethenyl, 1-propenyl or 2-propenyl; or phenyl (optionally substituted at arbitrary positions with halogen such as fluorine, chlorine or bromine; $C_{1-6}$ alkyl such as methyl or ethyl; or $C_{1-6}$ alkoxy such as methoxy or ethoxy).

n is 1, 2 or 3; m is 3, 4 or 5.

$R_1$ is hydrogen or $C_{1-6}$ alkyl such as methyl, ethyl, propyl, isopropyl, butyl, isobutyl, s-butyl or t-butyl.

$R_2$ is $C_{3-8}$ cycloalkyl (optionally substituted at arbitrary positions with halogen such as fluorine, chlorine or bromine; $C_{1-6}$ alkyl such as methyl or ethyl; or $C_{1-6}$ alkoxy such as methoxy or ethoxy); phenyl (optionally substituted at arbitrary positions with halogen such as fluorine, chlorine or bromine; $C_{1-6}$ alkyl such as methyl or ethyl; $C_{1-6}$ alkoxy such as methoxy or ethoxy; or $C_{1-2}$ alkylenedioxy such as metyhylenedioxy or ethylenedioxy), or a saturated or unsaturated heterocyclic group containing 1 to 4 N, O or S atoms (optionally substituted at arbitrary positions with halogen such as fluorine, chlorine or bromine; $C_{1-6}$ alkyl such as methyl or ethyl; $C_{1-6}$ haloalkyl such as chloromethyl, dichloromethyl, trichloromethyl, fluoromethyl, difluoromethyl or trifluoromethyl; $C_{1-6}$ alkoxy such as methoxy or ethoxy; or $C_{1-6}$ alkoxycarbonyl such as methoxycarbonyl or ethoxycarbonyl), such as furyl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl.

$R_3$ is a saturated or unsaturated heterocyclic group containing 1 to 4 N, O or S atoms (optionally substituted at arbitrary positions with halogen such as fluorine, chlorine or bromine; $C_{1-6}$ alkyl such as methyl or ethyl; $C_{1-6}$ alkoxy such as methoxy or ethoxy; $C_{1-6}$ alkoxycarbonyl such as methoxycarbonyl or ethoxycarbonyl; or $C_{1-6}$ haloalkyl such as chloromethyl, dichloromethyl, trichloromethyl, fluoromethyl, difluoromethyl or trifluoromethyl), such as furyl, thienyl, tetrahydrofuranyl, tetrahydrothienyl, pyrrolyl, pyrrolidinyl, imidazolyl, pyrazolyl, oxazolyl, isoxazolyl, thiazolyl, isothiazolyl, imidazolyl, triazolyl, oxadiazolyl, pyridyl, piperidinyl, piperazinyl, pyrimidyl or pyridazinyl; or a group represented by Formula $(CH_2)_kC(=O)R_4$.

$R_4$ is hydroxy; $C_{1-6}$ alkoxy such as methoxy or ethoxy; phenoxy (optionally substituted at arbitrary positions with halogen such as fluorine, chlorine or bromine; $C_{1-6}$ alkyl such as methyl or ethyl; $C_{1-6}$ alkoxy such as methoxy or ethoxy; $C_{1-6}$ alkoxycarbonyl such as methoxycarbonyl or ethoxycarbonyl; or $C_{1-6}$ haloalkyl such as chloromethyl, dichloromethyl, trichloromethyl, fluoromethyl, difluoromethyl or trifluoromethyl); benzyloxy (optionally substituted at arbitrary positions with halogen such as fluorine, chlorine or bromine; $C_{1-6}$ alkyl such as methyl or ethyl; $C_{1-6}$ alkoxy such as methoxy or ethoxy; $C_{1-6}$ alkoxycarbonyl such as methoxycarbonyl or ethoxycarbonyl; or $C_{1-6}$ haloalkyl such as chloromethyl, dichloromethyl, trichloromethyl, fluoromethyl, difluoromethyl or trifluoromethyl), or a group represented by Formula $Nr_6r_7$ or $NHNr_8r_9$.

$r_6$ and $r_8$ are hydrogen or $C_{1-6}$ alkyl such as methyl or ethyl.

$r_7$ and $r_9$ are hydrogen; $C_{3-6}$ cycloalkyl such as cyclopropyl, cyclobutyl, cyclopentyl or cyclohexyl; $C_{1-6}$ alkyl such as methyl, ethyl, propyl, isopropyl or butyl; $C_{1-6}$ alkoxycarbonyl $C_{1-6}$ alkyl such as methoxycarbonylmethyl, ethoxycarbonylmethyl, methoxycarbonylethyl or ethoxycarbonylethyl; $C_{1-6}$ alkyl, such as methyl or ethyl, substituted with a saturated or unsaturated L heterocyclic group containing 1 to 4 N, O or S atoms (which is optionally substituted at arbitrary positions with halogen such as fluorine, chlorine or bromine; $C_{1-6}$ alkyl such as methyl or ethyl; $C_{1-6}$ alkoxy such as methoxy or ethoxy; $C_{1-6}$ alkoxycarbonyl such as methoxycarbonyl or ethoxycarbonyl; or $C_{1-6}$ haloalkyl such as chloromethyl, dichloromethyl, trichloromethyl, fluoromethyl, difluoromethyl or trifluoromethyl), such as furyl, thienyl, tetrahydrofuranyl, tetrahydrothienyl, pyrrolyl, pyrrolidinyl, imidazolyl, pyrazolyl, oxazolyl, isoxazolyl, thiazolyl, isothiazolyl, imidazolyl, triazolyl, oxadiazolyl, pyridyl, piperidinyl, piperazinyl, pyrimidyl or pyridazinyl; phenyl (optionally substituted at arbitrary positions with halogen such as fluorine, chlorine or bromine; $C_{1-6}$ alkyl such as methyl or ethyl; or $C_{1-6}$ alkoxy such as methoxy or ethoxy); benzyl (optionally substituted at arbitrary positions with halogen such as fluorine, chlorine or bromine; $C_{1-6}$ alkyl such as methyl or ethyl; or $C_{1-6}$ alkoxy such as methoxy or ethoxy); or a saturated or unsaturated heterocyclic group containing 1 to 4 N, O or S atoms (optionally substituted at arbitrary positions with halogen such as fluorine, chlorine or bromine; $C_{1-6}$ alkyl such as methyl or ethyl; $C_{1-6}$ alkoxy such as methoxy or ethoxy; $C_{1-6}$ alkoxycarbonyl such as methoxycarbonyl or ethoxycarbonyl; or $C_{1-6}$ haloalkyl such as chloromethyl, dichloromethyl, trichloromethyl, fluoromethyl, difluoromethyl or trifluoromethyl), such as furyl, thienyl, tetrahydrofuranyl, tetrahydrothienyl, pyrrolyl, pyrrolidinyl, imidazolyl, pyrazolyl, oxazolyl, isoxazolyl, thiazolyl, isothiazolyl, imidazolyl, triazolyl, oxadiazolyl, pyridyl, piperidinyl, piperazinyl, pyrimidyl or pyridazinyl.

$r_6$ and $r_7$ may join, together with N, to form a ring

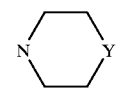

(wherein, Y is O, $CH_2$ or $Nr_{10}$).

$r_{10}$ is hydrogen, $C_{1-6}$ alkyl such as methyl or ethyl, phenyl, or benzyl.

k is 0, 1 or 2.

The substituents may be the same or different, if the said phenyl, benzyl and heterocyclic groups have two or more of them.

Examples of pharmaceutically acceptable salts include salts of inorganic acids such as hydrochloric acid, sulfuric acid, nitric acid and phosphoric acid and of organic acids such as acetic acid, propionic acid, lactic acid, succinic acid, tartaric acid, citric acid, benzoic acid, salicylic acid, nicotinic acid and heptagluconic acid, of compounds of Formula (1).

In the compounds of the present invention, the carbon of $CHR_1R_2$ may become asymmetric, depending on what kind of groups $R_1$ and $R_2$ are. The present invention covers optically active compounds as well as racemic ones.

Processes of the present invention and processes for the preparation of novel compounds which may become intermediates or others are described below.

Process 1

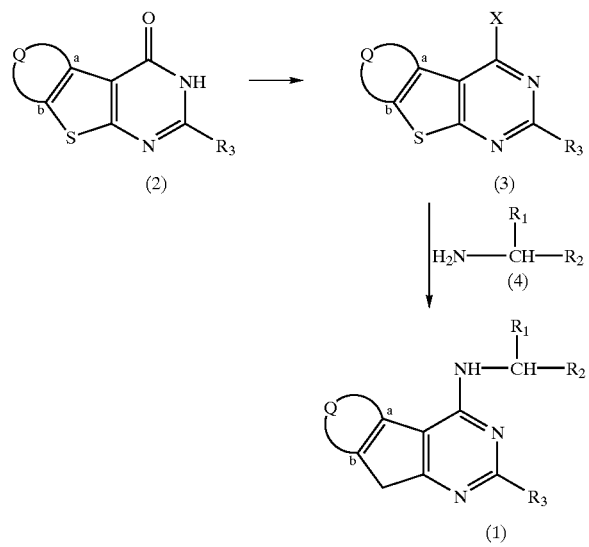

(Wherein, Q, $R_1$, $R_2$ and $R_3$ are as defined above and X is halogen.)

Target compound (1) is obtained by a substitution reaction of Compound (3) and Compound (4) in a solvent according to an ordinary method.

There are no particular restrictions on solvents used, if inert to the reaction. Examples of solvents used include ethers such as diethyl ether, tetrahydrofuran (THF) and 1,4-dioxane; aromatic hydrocarbons such as benzene, toluene and xylene; halogenated hydrocarbons such as dichloromethane, chloroform and 1,2-dichloroethane; and pyridine, acetonitrile, dimethylformamide (DMF) and dimethylsulfoxide (DMSO).

Reaction temperature is about −15° C. to the boiling point of a solvent used, preferably 0 to 80° C.

Halogenation of thienopyrimidone of Compound (2) gives Compound (3). Examples of halogen X include chlorine and bromine.

The halogenation reaction is carried out by an ordinary method. For example, in the case of chlorination, a method is applied of using phosphorus oxychloride, phosphorus pentachloride, thionyl chloride or the like as a chlorinating agent.

There are no particular restrictions on solvents used, if inert to the reaction. Examples of solvents used include aromatic hydrocarbons such as benzene, toluene and xylene; halogenated hydrocarbons such as dichloromethane, chloroform and 1,2-dichloroethane; and acetonitrile, DMF and DMSO.

Reaction temperature is about −15° C. to the boiling point of a solvent used, preferably 20° C. to the boiling point of a solvent.

A starting material, thienopyrimidone of Compound (2), can be prepared according to known methods disclosed in papers, for example, J. Het. Chem., 21, 375–380 (1984) or Indian J. Chem., 28B (12) 1039–1047 (1989).

A starting material, Compound (4), is also prepared according to known methods disclosed in papers, for example, J. Med. Chem., 41, 3367–3372 (1998).

Process 2

A compound of the said Formula (1) where $R^3$ is $CONr_4r_5$ can also be prepared according to following reaction equation:

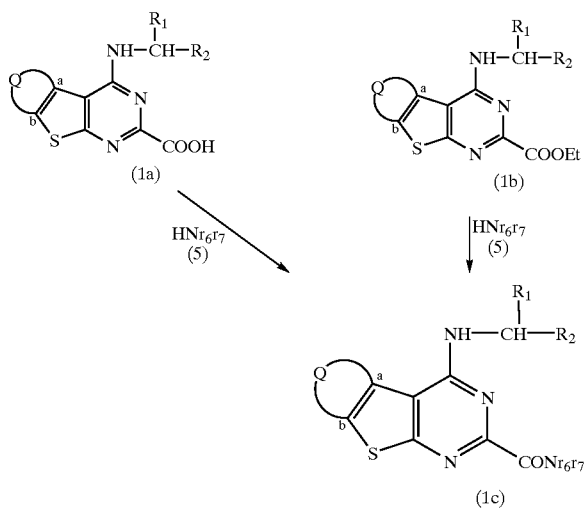

(Wherein Q, $R^1$, $R^2$, $r_6$ and $r_7$ are as defined above.)

Dehydration condensation of Compound (1a) and Compound (5) by an ordinary method gives Compound (1c).

There are no particular restrictions on the dehydration condensation reaction, if an ordinary method is applied. A method of using a condensing agent is preferred.

Examples of condensing agents used include 1,3-dicyclohexylcarbodiimide, 1-(3-dimethylaminopropyl)-3-ethylcarbodiimide and 2-ethoxy-1-ethoxycarbonyl-1,2-dihydroquinoline.

This reaction proceeds more promptly if N-hydroxysuccinimide, 1-hydroxybenzotriazole or 3,4-dihydro-3-hydroxy-4-oxo-1,2,3-benzotriazine coexists. There are no particular restrictions on solvents used, if inert to the reaction. Examples of solvents used include ethers such as diethyl ether, THF and 1,4-dioxane; aromatic hydrocarbons such as benzene, toluene and xylene; halogenated hydrocarbons such as dichloromethane, chloroform and 1,2-dichloroethane; and acetonitrile, DMF, DMSO and pyridine.

Reaction temperature is about −15° C. to the boiling point of a solvent used, preferably 0 to 80° C.

An amido derivative of Formula (1c) can also be prepared from Compound (1b).

The reaction is carried out without a solvent or using a solvent including an alcohol such as methanol, ethanol or propanol; halogenated hydrocarbon such as dichloromethane, chloroform or 1,2-dichloroethane; acetonitrile, DMF or DMSO, at a reaction temperature from −15 to 200° C., preferably 0 to 150° C.

Process 3

(Wherein, $R_1$, $R_2$, $R_3$, $r_2$, $r_3$ and $r_4$ are as defined above.)

Compound (1f) can be prepared by Process 1, and also by acylation of Compound (1e) as shown in the above reaction equation.

There are no particular restrictions on the acylation reaction, if an ordinary method is applied. The compound can be prepared using an acid chloride of Compound (6).

In this case, the reaction proceeds more promptly if a base coexists.

Examples of bases used include inorganic bases such as sodium hydrogen carbonate and potassium carbonate, and amines such as triethylamine and pyridine.

There are no particular restrictions on solvents used, if inert to the reaction. Examples of solvents used include ethers such as diethyl ether, THF and 1,4-dioxane; aromatic hydrocarbons such as benzene, toluene and xylene; halogenated hydrocarbons such as dichloromethane, chloroform and 1,2-dichloroethane; and acetonitrile, DMF and DMSO.

Reaction temperature is about −15° C. to the boiling point of a solvent used, preferably 0 to 80° C.

Compound (1e) can be obtained by hydrolysis of an N-ethoxycarbonyl compound (1d) prepared in Process 1.

There are no particular restrictions on the hydrolysis reaction, if an ordinary method is applied. The reaction proceeds promptly if a base is added.

Preferred bases used include inorganic bases such as sodium hydroxide and potassium hydroxide.

In this reaction, the coexistence of hydrazine hydrate may increase reaction yield.

Examples of solvents used include alcohols such as methanol, ethanol and ethylene glycol; ethers such as THF and dioxane; and DMF and DMSO.

Reaction temperature is about 0° C. to the boiling point of a solvent used, preferably 20° C. to the boiling point of a solvent used.

Compound (1) of the present invention may have asymmetric carbons, depending on groups of $R_1$ and $R_2$ or $r_2$ and $r_3$ in Formula (1), so that there may exist optical isomers. It goes without saying that the present invention covers these isomers.

In the present invention, usual post-treatments give target compounds after the completion of the reactions.

The structures of the compounds of the present invention were determined by IR, NMR, MS and other means.

Best Forms to Implement the Invention

The present invention is described in more detail in reference to Examples.

EXAMPLE 1

Preparation of 5,6,7,8-tetrahydro-4-[(3-chloro-4-methoxy)benzylamino]-7-ethoxycarbonyl-2-(3-pyridyl)pyrido[4',3':4,5]thieno[2,3-d]pyrimidine (Compound No. 1-15)

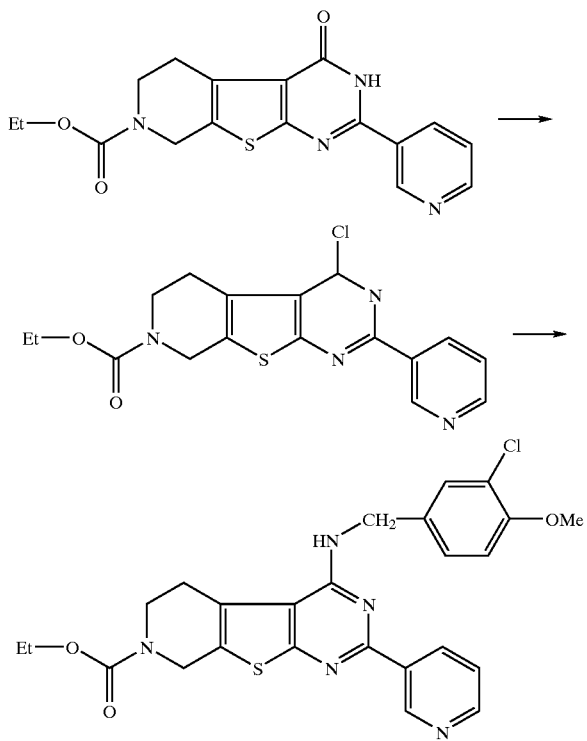

4.1 g of 5,6,7,8-tetrahydro-4-oxo-7-ethoxycarbonyl-2-(3-pyridyl)pyrido[4',3':4,5]thieno[2,3-d]pyrimidine was added to 40 ml of phosphorus oxychloride, and stirred at 80 to 100° C. for 3 hours. After phosphorus oxychloride was distilled off under reduced pressure, 50 ml of water was added to the reaction residue. The reaction solution was made alkaline with an aqueous saturated solution of sodium hydrogen carbonate while cooling, and extracted with chloroform. The organic layer was washed with saturated salt water and dried over anhydrous magnesium sulfate. Magnesium sulfate was filtered off. The filtrate was concentrated under reduced pressure to give 5.0 g of 5,6,7,8-tetrahydro-4-chloro-7-ethoxycarbonyl-2-(3-pyridyl)pyrido[4',3':4,5]thieno[2,3-d]pyrimidine.

To 5.0 g of 5,6,7,8-tetrahydro-4-chloro-7-ethoxycarbonyl-2-(3-pyridyl)pyrido[4',3':4,5]thieno[2,3-d]pyrimidine were added 50 ml of DMSO and 2.5 g of 3-chloro-4-methoxybenzylamine, and heated with stirring at 80° C. for 3 hours. The reaction solution was poured into water. The deposited crystals were separated by filtration and dried to give 4.2 g of the title compound. m.p. 223–225° C.

EXAMPLE 2

Preparation of 5,6,7,8-tetrahydro-4-[(3-chloro-4-methoxy)benzylamino]-2-(3-pyridyl)pyrido[4',3':4,5]thieno[2,3-d]pyrimidine (Compound No. 1-8)

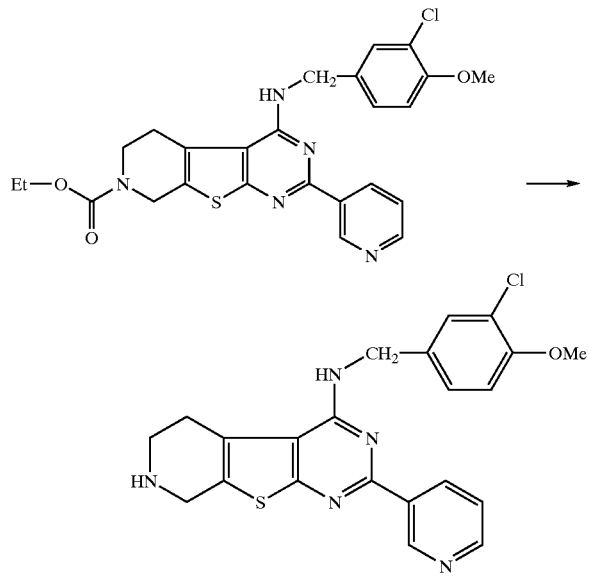

To 2 g of 5,6,7,8-tetrahydro-4-[(3-chloro-4-methoxy)benzylamino]-7-ethoxycarbonyl-2-(3-pyridyl)pyrido[4',3':4,5]thieno[2,3-d]pyrimidine obtained in Example 1 were added 40 ml of ethylene glycol, 5 g of potassium hydroxide and 4 ml of hydrazine hydrate, and heated at reflux for 2 hours. The reaction solution was poured into water. The deposited crystals were separated by filtration, washed with water and ethyl acetate, and dried to give 1.4 g of the title compound. m.p. 135–139° C.

EXAMPLE 3

Preparation of 5,6,7,8-tetrahydro-4-[(3-chloro-4-methoxy)benzylamino]-7-acetyl-2-(3-pyridyl)pyrido[4',3':4,5]thieno[2,3-d]pyrimidine (Compound No. 1-9)

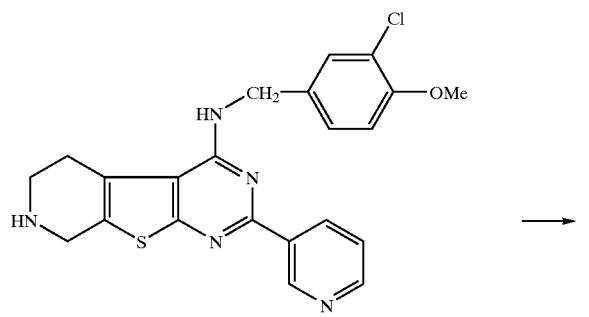

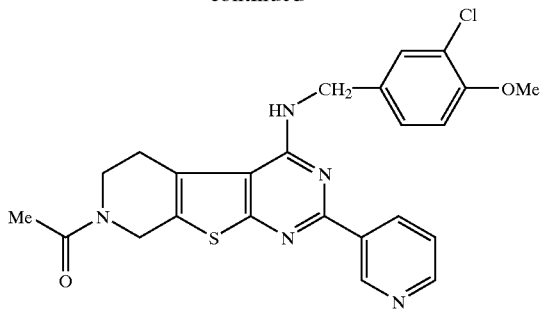

To 0.3 g of 5,6,7,8-tetrahydro-4-[(3-chloro-4-methoxy) benzylamino]-2-(3-pyridyl)pyrido[4',3':4,5]thieno[2,3-d] pyrimidine were added 20 ml of chloroform and 0.3 g of triethylamine, and, while cooling with ice, 0.06 g of acetyl chloride was added. The solution was returned to room temperature and stirred for an hour. Water was added to the reaction solution to extract with chloroform. The organic layer was washed with saturated salt water and dried over anhydrous magnesium sulfate. After magnesium sulfate was filtered off, chloroform was concentrated under reduced pressure. The residue was purified with silica gel column chromatography (chloroform:methanol=100:1) to give 0.1 g of the title compound. m.p. 225–227° C.

EXAMPLE 4

Preparation of ethyl 5,6,7,8-tetrahydro-4-[(3-chloro-4-methoxy)benzylamino]-7-methylpyrido[4',3':4,5]thieno[2,3-d]pyrimidine-2-carboxylate (Compound No. 1-69)

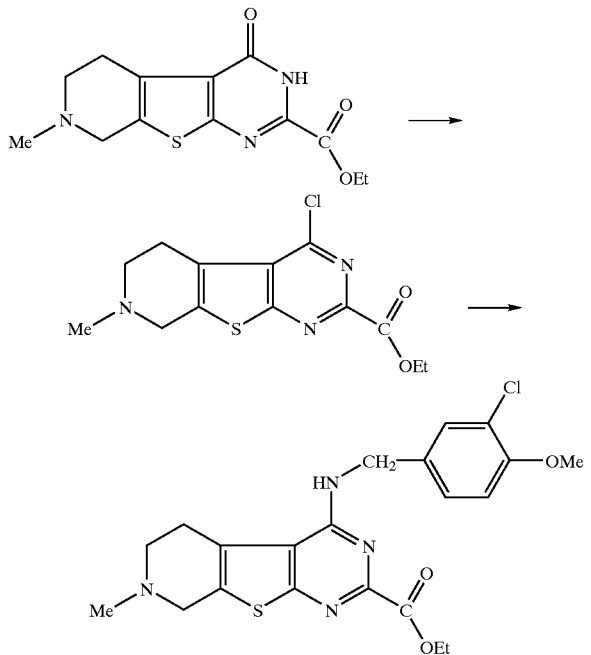

10 g of ethyl 5,6,7,8-tetrahydro-4-oxo-7-methylpyrido[4',3':4,5]thieno[2,3-d]pyrimidine-2-carboxylate was added to 60 ml of phosphorus oxychloride, and stirred at 80 to 100° C. for 3 hours. After phosphorus oxychloride was distilled off under reduced pressure, 100 ml of cool water was added to the reaction residue. The reaction solution was made alkaline with an aqueous saturated solution of sodium hydrogen carbonate, and extracted with chloroform. The organic layer was washed with saturated salt water and dried over anhydrous magnesium sulfate. After magnesium sulfate was filtered off, the filtrate was concentrated under reduced pressure to give 9.5 g of ethyl 5,6,7,8-tetrahydro-4-chloro-7-methylpyrido[4',3':4,5]thieno[2,3-d]pyrimidine-2-carboxylate.

To 9.5 g of ethyl 5,6,7,8-tetrahydro-4-chloro-7-methylpyrido[4',3':4,5]thieno[2,3-d]pyrimidine-2-carboxylate were added 100 ml of DMSO and 8.1 g of 3-chloro-4-methoxybenzylamine, and heated with stirring at 80° C. for 3 hours. The reaction solution was poured into water and extracted with ethyl acetate. The organic layer was washed with saturated salt water and dried over anhydrous magnesium sulfate. After magnesium sulfate was filtered off, the filtrate was concentrated under reduced pressure. The residue was purified with silica gel column chromatography to give 9.3 g of the title compound. m.p. 175–176° C.

EXAMPLE 5

Preparation of 5,6,7,8-tetrahydro-4-[(3-chloro-4-methoxy)benzylamino]-7-methylpyrido[4',3':4,5]thieno[2,3-d]pyrimidine-2-carboxylic acid (Compound No. 1-71)

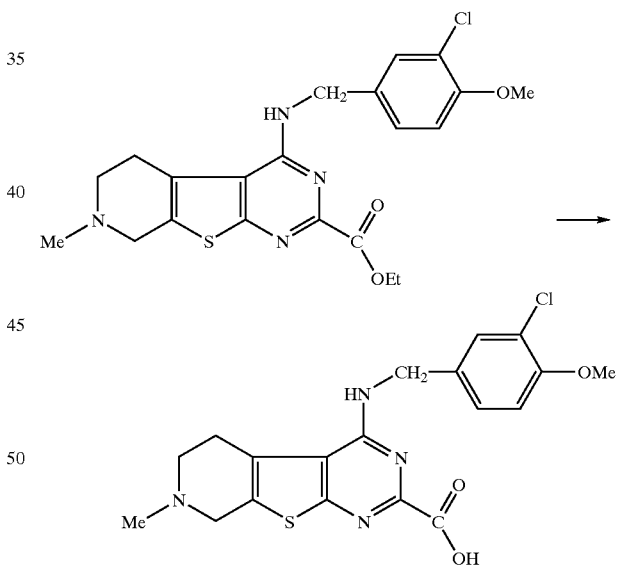

To 9.3 g of ethyl 5,6,7,8-tetrahydro-4-[(3-chloro-4-methoxy)benzylamino]-7-methylpyrido[4',3':4,5]thieno[2,3-d]pyrimidine-2-carboxylate were added 30 ml of ethanol, 20 ml of water and 1.7 g of sodium hydroxide, and stirred at 60° C. for 2 hours. The reaction solution was concentrated under reduced pressure and made pH 8 with 2N-hydrochloric acid. The deposited crystals were separated by filtration, washed with water and ethyl acetate, and air-dried to give 7.5 g of the title compound. 270° C. decomposition.

EXAMPLE 6

Preparation of 5,6,7,8-tetrahydro-4-[(3-chloro-4-methoxy)benzylamino]-7-methylpyrido[4',3':4,5]thieno[2,3-d]pyrimidine-2-N-(4-chlorophenyl)carboxamide (Compound No. 1-61)

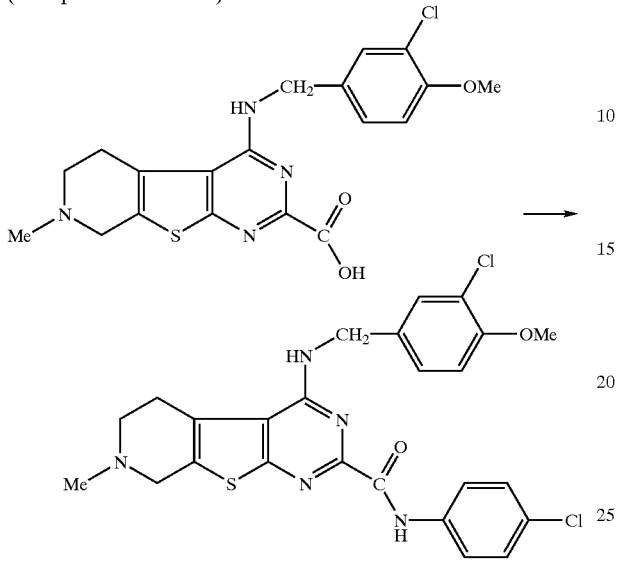

To 0.3 g of 5,6,7,8-tetrahydro-4-[(3-chloro-4-methoxy)benzyl]-7-methylpyrido[4',3':4,5]thieno[2,3-d]pyrimidine-2-carboxylic acid were added 0.16 g of 1-(3-dimethylaminopropyl)-3-ethylcarbodiimide hydrochloride, 0.12 g of 1-hydroxybenzotriazole hydrochloride, 0.1 g of triethylamine, 0.09 g of 4-chloroaniline and 20 ml of DMF, and stirred at room temperature for 20 hours. The reaction solution was poured into water. The deposited crystals were separated by filtration and washed with water and ethyl acetate to give 0.22 g of the title compound. 222° C. decomposition.

EXAMPLE 7

Preparation of 5,6,7,8-tetrahydro-4-[(3-chloro-4-methoxy)benzyl]-7-methylpyrido[4',3':4,5]thieno[2,3-d]pyrimidine-2-carboxamide (Compound No. 1-83)

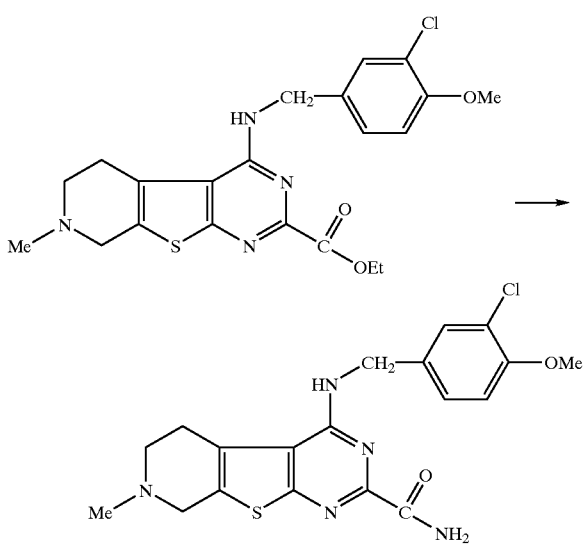

0.3 g of ethyl 5,6,7,8-tetrahydro-4-[(3-chloro-4-methoxy)benzyl]-7-methylpyrido[4',3':4,5]thieno[2,3-d]pyrimidine-2-carboxylate and 40 ml of ethanol saturated with ammonia were heated with stirring in an autoclave at 120 to 140° C. for 4 hours. After cooled, the deposited crystals were separated by filtration, and dried to give 0.2 g of the title compound. 230° C. decomposition.

EXAMPLE 8

Preparation of 5,6,7,8-tetrahydro-4-[(3-chloro-4-methoxy)benzylamino]-7-methyl-2-(pyrazol-3-yl)pyrido[4',3':4,5]thieno[2,3-d]pyrimidine (Compound No. 1-43)

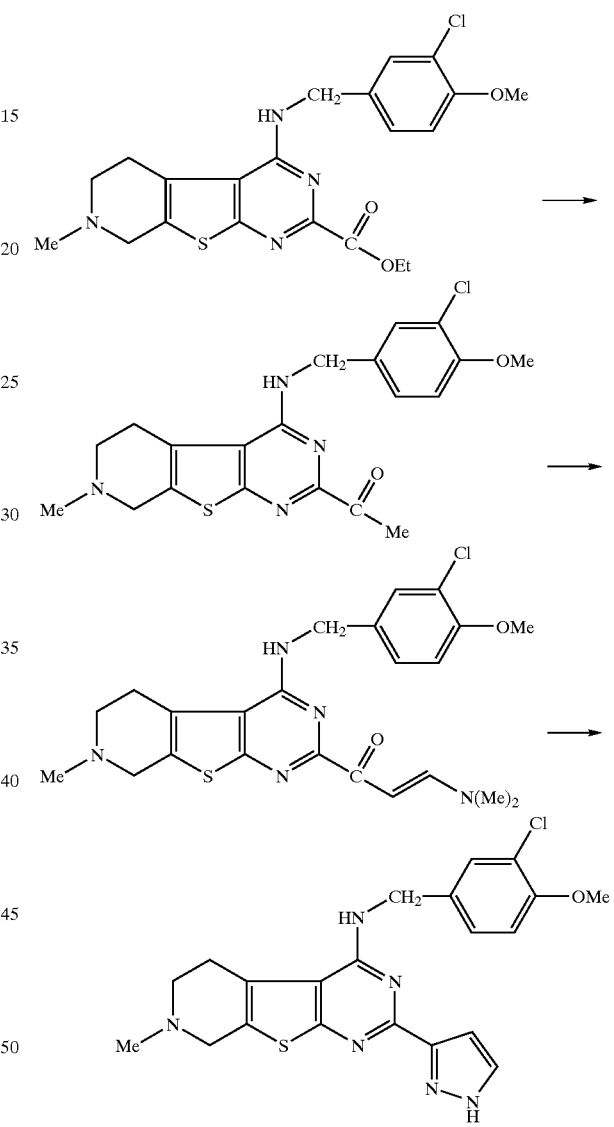

45 ml of THF was added to 2 g of ethyl 5,6,7,8-tetrahydro-4-[(3-chloro-4-methoxy)benzylamino]-7-methylpyrido[4',3':4,5]thieno[2,3-d]pyrimidine-2-carboxylate under nitrogen gas stream, and cooled to −70° C. To the resulting solution was added 8.72 ml of a 1-mol/ml ether solution of methyl magnesium bromide, and stirred at −40° C. for 4 hours. The reaction solution was poured into water and extracted with ethyl acetate. The organic layer was washed with saturated salt water and dried over anhydrous magnesium sulfate. After magnesium sulfate was filtered off, the solvent was distilled off under reduced pressure. The obtained crystals were washed with a mixed solution of ethyl acetate and diethyl ether to give 1.7 g of 5,6,7,8- tetrahydro-4-[(3-chloro-4-methoxy)benzylamino]-7-methyl-2-acetylpyrido[4',3':4,5]thieno[2,3-d]pyrimidine.

1.7 g of 5,6,7,8-tetrahydro-4-[(3-chloro-4-methoxy)benzylamino]-7-methyl-2-acetylpyrido[4',3':4,5]thieno[2,3-d]pyrimidine was dissolved in 20 ml of dimethylformamide dimethyl acetal, and stirred for 10 hours. The reaction solution was concentrated under reduced pressure. The obtained crystals were washed with diethyl ether to give 1.0 g of (2E)-3-(dimethylamino)-1-[7-methyl-4-[(3-chloro-4-methoxy)benzylamino]-5,6,7,8-tetrahydropyrido[4',3':4,5]thieno[2,3-d]pyrimidin-2-yl]]propo-2-ene-1-one.

0.3 g of (2E)-3-(dimethylamino)-1-[7-methyl-4-[(3-chloro-4-methoxy)benzylamino]-5,6,7,8-tetrahydropyrido[4',3':4,5]thieno[2,3-d]pyrimidin-2-yl]]propo-2-ene-1-one was dissolved in 5 ml of ethanol. To the resulting solution were added 0.03 g of hydrazine hydrate and 0.03 g of a 2N aqueous solution of sodium hydroxide, and stirred at room temperature for 6 hours. After the reaction solution was concentrated under reduced pressure, chloroform was added. The resulting solution was washed with saturated salt water and dried over anhydrous magnesium sulfate. After magnesium sulfate was filtered off, the solvent was concentrated under reduced pressure. The residue was purified with silica gel column chromatography (chloroform:methanol=50:1) to give 0.07 g of the title compound.

EXAMPLE 9

Preparation of 5,6,7,8-tetrahydro-4-[(3-chloro-4-methoxy)benzylamino]-7-methyl-2-(3-methyl-1,2,4-oxadiazol-5-yl)pyrido[4',3':4,5]thieno[2,3-d]pyrimidine (Compound No. 1-40)

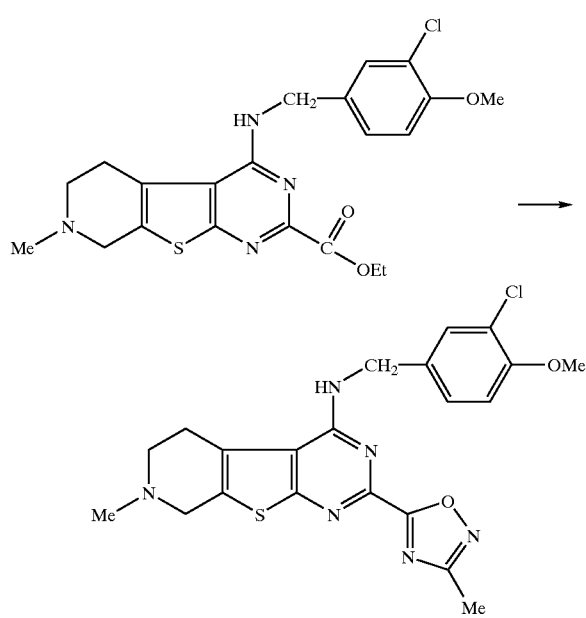

0.12 g of acetamidoxime was dissolved in 10 ml of THF, and 0.1 g of molecular sieves 4A and 0.06 g of sodium hydride were added. To the resulting solution was added 0.5 g of ethyl 5,6,7,8-tetrahydro-4-[(3-chloro-4-methoxy)benzylamino]-7-methylpyrido[4',3':4,5]thieno[2,3-d]pyrimidine-2-carboxylate, and heated at reflux with stirring for 2 hours. The reaction solution was poured into water. The deposited crystals were separated by filtration and dried to give 0.17 g of the title compound. 210° C. decomposition.

EXAMPLE 10

Preparation of 5,6,7,8-tetrahydro-4-[(3-chloro-4-methoxy)benzylamino]-7-methyl-2-(1,3,4-oxadiazol-2-yl)pyrido[4',3':4,5]thieno[2,3-d]pyrimidine (Compound No. 1-45)

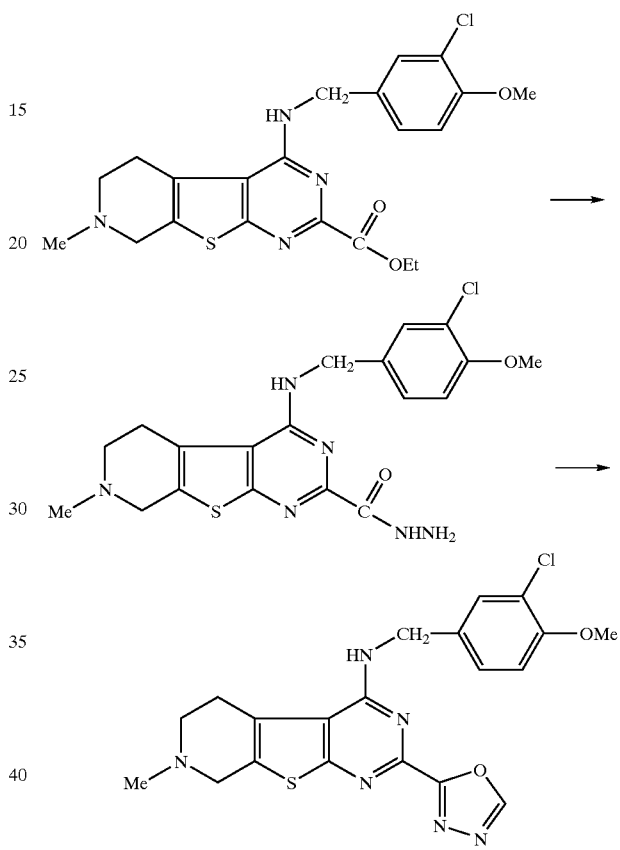

1 g of ethyl 5,6,7,8-tetrahydro-4-[(3-chloro-4-methoxy)benzylamino]-7-methylpyrido[4',3':4,5]thieno[2,3-d]pyrimidine-2-carboxylate and 0.15 g of hydrazine hydrate were dissolved in 20 ml of ethanol, and heated at reflux with stirring for 4 hours. The reaction solution was concentrated under reduced pressure. The obtained crystals were washed with chloroform and ethyl acetate, and dried to give 0.6 g of 5,6,7,8-tetrahydro-4-[(3-chloro-4-methoxy)benzylamino]-7-methylpyrido[4',3':4,5]thieno[2,3-d]pyrimidin-2-yl-N-aminocarboxamide.

0.5 g of 5,6,7,8-tetrahydro-4-[(3-chloro-4-methoxy)benzylamino]-7-methylpyrido[4',3':4,5]thieno[2,3-d]pyrimidin-2-yl-N-aminocarboxamide was dissolved in 10 ml of ethyl ortho-formate, and a catalytic amount (0.5 to 5%) of p-toluenesulfonic acid was added to stir at 50° C. for 2 hours. The reaction solution was concentrated under reduced pressure and water was added. The resulting solution was extracted with chloroform. The organic layer was concentrated under reduced pressure. The residue was purified with silica gel column chromatography (chloroform:methanol=50:1) to give 0.03 g of the title compound. m.p. 160–163° C.

EXAMPLE 11

Preparation of 5,6,7,8-tetrahydro-4-[(3-chloro-4-ethoxy)benzylamino]-7-methyl-2-(oxazol-5-yl)pyrido[4',3':4,5]thieno[2,3-d]pyrimidine (Compound No. 1-44)

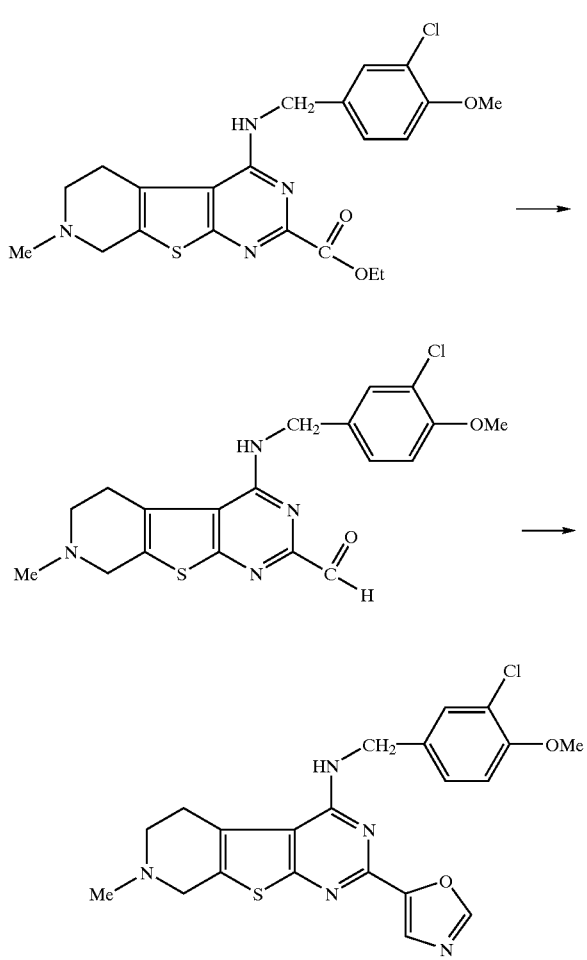

EXAMPLE 12

Preparation of 5,6,7,8-tetrahydro-4-[(3-chloro-4-methoxy)benzylamino]-7-methyl-2-(1-imidazolylmethyl)pyrido[4',3':4,5]thieno[2,3-d]pyrimidine (Compound No. 1-42)

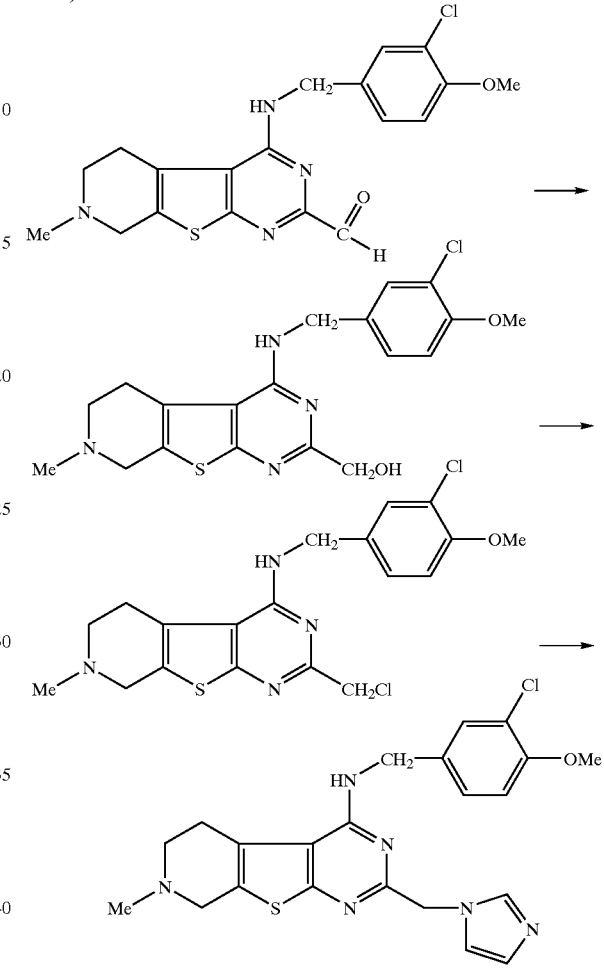

2 g of ethyl 5,6,7,8-tetrahydro-4-[(3-chloro-4-methoxy)benzylamino]-7-methylpyrido[4',3':4,5]thieno[2,3-d]pyrimidine-2-carboxylate was dissolved in 50 ml of THF under nitrogen gas stream, and cooled to −20° C. To the resulting solution was added 8.72 ml of 1 mol/ml of DIBAL-H (diisobutyl aluminum hydride) and stirred at −40° C. for 4 hours. The reaction solution was poured into water and extracted with ethyl acetate. The organic layer was dried over anhydrous magnesium sulfate. Magnesium sulfate was filtered off. The solvent was concentrated under reduced pressure to give 1.5 g of 5,6,7,8-tetrahydro-4-[(3-chloro-4-methoxy)benzylamino]-7-methylpyrido[4',3':4,5]thieno[2,3-d]pyrimidine-2-carboaldehyde.

0.3 g of 5,6,7,8-tetrahydro-4-[(3-chloro-4-methoxy)benzylamino]-7-methylpyrido[4',3':4,5]thieno[2,3-d]pyrimidine-2-carboaldehyde was dissolved in 10 ml of methanol. To the resulting solution were added 0.12 g of potassium carbonate and 0.15 g of (p-toluenesulfonyl)methylisocyanide, and heated at reflux with stirring for 4 hours. After the reaction solution was concentrated under reduced pressure, water was added. The deposited crystals were separated by filtration to give 0.27 g of the title compound.

1 g of 5,6,7,8-tetrahydro-4-[(3-chloro-4-methoxy)benzylamino]-7-methylpyrido[4',3':4,5]thieno[2,3-d]pyrimidine-2-carboaldehyde was dissolved in 10 ml of ethanol, and 0.1 g of sodium borohydride was added to stir at room temperature for 2 hours. The reaction solution was concentrated under reduced pressure and water was added. The resulting solution was extracted with chloroform. The organic layer was washed with saturated salt water and dried over anhydrous magnesium sulfate. After magnesium sulfate was filtered off, the filtrate was concentrated under reduced pressure to give 0.75 g of 5,6,7,8-tetrahydro-4-[(3-chloro-4-methoxy)benzylamino]-7-methyl-2-hydroxymethylpyrido[4',3':4,5]thieno[2,3-d]pyrimidine.

0.75 g of 5,6,7,8-tetrahydro-4-[(3-chloro-4-methoxy)benzylamino]-7-methyl-2-hydroxymethylpyrido[4',3':4,5]thieno[2,3-d]pyrimidine was dissolved in 10 ml of benzene, and water was added. The deposited crystals were separated by filtration to give 0.6 g of 5,6,7,8-tetrahydro-4-[(3-chloro-4-methoxy)benzylamino]-7-methyl-2-chloromethylpyrido[4',3':4,5]thieno[2,3-d]pyrimidine.

0.02 g of sodium hydride was added to a solution of 0.03 g of imidazole added to 5 ml of dimethylformamide, and stirred at 60° C. for 30 minutes. To the resulting solution was added 0.2 g of 5,6,7,8-tetrahydro-4-[(3-chloro-4-methoxy)

benzylamino]-7-methyl-2-chloromethylpyrido[4',3':4,5]thieno[2,3-d]pyrimidine, and stirred at 60° C. for 2 hours. The reaction solution was poured into water and extracted with ethyl acetate. The organic layer was washed with saturated salt water and dried over anhydrous magnesium sulfate. After magnesium sulfate was filtered off, the filtrate was concentrated under reduced pressure. The residue was purified with silica gel column chromatography (chloroform:methanol=50:1) to give 0.1 g of the title compound. Refer to Table 4 for NMR data.

Representative examples of the compounds of the present invention, including those of the above examples, are shown in Tables 1 to 3.

Abbreviations in the tables have the following meanings:

Me: methyl, Et: ethyl, Pr: propyl, i: iso, c: cyclo, Ph: phenyl

NMR data of the compounds in the tables are shown in Table 4.

TABLE 1

[Structure: pyrido-thieno-pyrimidine core with substituents r1 (on N), r2 and r3 (on adjacent C), NH–CH(R1)–R2 at 4-position, and R3 at 2-position]

| Compd. No. | $r_1$ | $r_2$ | $r_3$ | $R_1$ | $R_2$ | $R_3$ | Phys. Const. []: m.p. °C. |
|---|---|---|---|---|---|---|---|
| 1-1 | CH$_2$Ph | H | H | H | 2-Cl-4-(position)-OMe-phenyl | benzo[1,3]dioxol-5-yl | [218] |
| 1-2 | COOEt | H | H | H | benzo[1,3]dioxol-5-yl | pyridin-4-yl | NMR |
| 1-3 | H | H | H | H | 2-Cl-4-OMe-phenyl | pyridin-4-yl | [198–200] |
| 1-4 | CH$_2$Ph | H | H | H | 2-Cl-4-OMe-phenyl | pyridin-3-yl | [165]dec. |
| 1-5 | COOEt | H | H | H | 2-Cl-4-OMe-phenyl | pyridin-4-yl | [218–220] |
| 1-6 | Me | H | H | H | 2-Cl-4-OMe-phenyl | furan-2-yl | [90–92] |
| 1-7 | Me | H | H | H | 2-Cl-4-OMe-phenyl | pyridin-4-yl | [118–120] |
| 1-8 | H | H | H | H | 2-Cl-4-OMe-phenyl | pyridin-3-yl | [135–139] |

TABLE 1-continued

| Compd. No. | r₁ | r₂ | r₃ | R₁ | R₂ | R₃ | Phys. Const. []: m. p. °C. |
|---|---|---|---|---|---|---|---|
| 1-9 | COMe | H | H | H | 3-Cl-4-OMe-phenyl | 3-pyridyl | [226–227] |
| 1-10 | Me | H | H | H | 3-Cl-4-OMe-phenyl | 1-(4-COOEt)piperidinyl | |
| 1-11 | Me | H | H | H | 3-Cl-4-OMe-phenyl | 1-imidazolyl | |
| 1-12 | Me | H | H | H | 3-Cl-4-OMe-phenyl | 1-(1,2,4-triazolyl) | |
| 1-13 | Me | H | H | H | 3-Cl-4-OMe-phenyl | 1-pyrazolyl | |
| 1-14 | Me | H | H | H | 3-Cl-4-OMe-phenyl | 2-Me-1-imidazolyl | |
| 1-15 | COOEt | H | H | H | 3-Cl-4-OMe-phenyl | 3-pyridyl | [223–225] |
| 1-16 | COOEt | H | H | H | 3-Cl-4-OMe-phenyl | 2-pyridyl | [157–159] |
| 1-17 | COOEt | H | H | H | 3-Cl-4-OMe-phenyl | 2-thienyl | |
| 1-18 | COOEt | H | H | H | 3-Cl-4-OMe-phenyl | 2-furyl | |

TABLE 1-continued
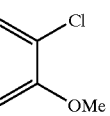
| Compd. No. | r₁ | r₂ | r₃ | R₁ | R₂ | R₃ | Phys. Const. []: m. p. °C. |
|---|---|---|---|---|---|---|---|
| 1-19 | COOEt | H | H | H | 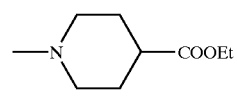 | 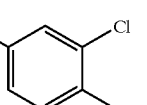 | |
| 1-20 | COOEt | H | H | H | 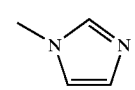 | 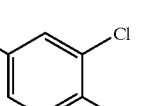 | |
| 1-21 | COOEt | H | H | H | 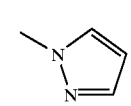 | 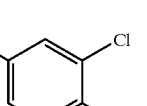 | |
| 1-22 | COOEt | H | H | H | 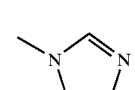 | 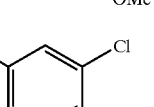 | |
| 1-23 | COOEt | H | H | H | 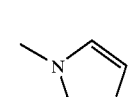 | 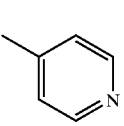 | |
| 1-24 | COOEt | H | H | H | 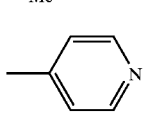 | 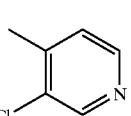 | |
| 1-25 | COOEt | H | H | H | 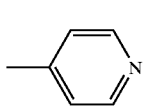 | 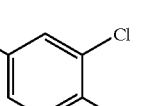 | |
| 1-26 | COOEt | H | H | H | 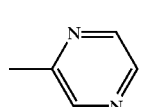 | 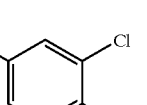 | [187–189] |
| 1-27 | Me | H | H | H | 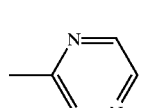 | 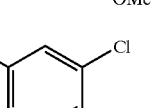 | |
| 1-28 | Me | H | H | H | 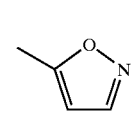 | | |

TABLE 1-continued

| Compd. No. | $r_1$ | $r_2$ | $r_3$ | $R_1$ | $R_2$ | $R_3$ | Phys. Const. []: m. p. °C. |
|---|---|---|---|---|---|---|---|
| 1-29 | COOEt | H | H | H | 3-Cl-4-OMe-phenyl | 5-methylisoxazol-3-yl | |
| 1-30 | COMe | H | H | H | 3-Cl-4-OMe-phenyl | 5-methylisoxazol-3-yl | |
| 1-31 | H | H | H | H | 3-Cl-4-OMe-phenyl | 5-methylisoxazol-3-yl | |
| 1-32 | H | H | H | H | 3-Cl-4-OMe-phenyl | 1-methylimidazol-2-yl | |
| 1-33 | COMe | H | H | H | 3-Cl-4-OMe-phenyl | 1-methylimidazol-2-yl | |
| 1-34 | COMe | H | H | H | 3-Cl-4-OMe-phenyl | 1-methylpyrazol-5-yl | |
| 1-35 | H | H | H | H | 3-Cl-4-OMe-phenyl | 1-methylpyrazol-5-yl | |
| 1-36 | H | H | H | H | 3-Cl-4-OMe-phenyl | methylpyrazinyl | |
| 1-37 | COMe | H | H | H | 3-Cl-4-OMe-phenyl | methylpyrazinyl | |
| 1-38 | H | H | H | H | 3-Cl-4-OMe-phenyl | 1-methyl-1,2,4-triazol-5-yl | |

TABLE 1-continued
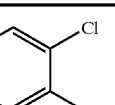
| Compd. No. | $r_1$ | $r_2$ | $r_3$ | $R_1$ | $R_2$ | $R_3$ | Phys. Const. []: m. p. °C. |
|---|---|---|---|---|---|---|---|
| 1-39 | COMe | H | H | H | 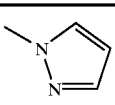 | 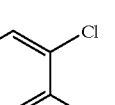 | |
| 1-40 | Me | H | H | H | 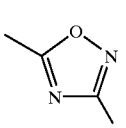 | 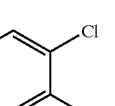 | [210]dec. |
| 1-41 | COOEt | H | H | H | 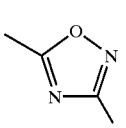 | 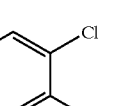 | [235–237] |
| 1-42 | Me | H | H | H | 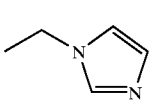 | 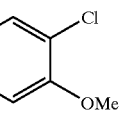 | NMR |
| 1-43 | Me | H | H | H | 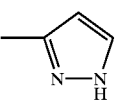 | 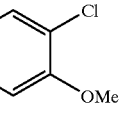 | NMR |
| 1-44 | Me | H | H | H | 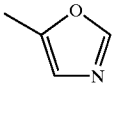 | 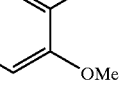 | NMR |
| 1-45 | Me | H | H | H | 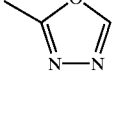 | 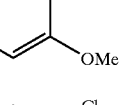 | [160–163] |
| 1-46 | COOMe | H | H | H | 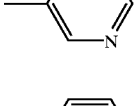 | 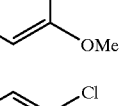 | [155–157] |
| 1-47 | H | H | H | H | 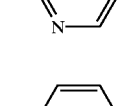 | 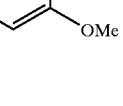 | [95–97] |
| 1-48 | CONHEt | H | H | H | 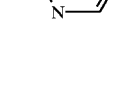 | | [210–212] |

TABLE 1-continued

| Compd. No. | r₁ | r₂ | r₃ | R₁ | R₂ | R₃ | Phys. Const. []: m. p. °C. |
|---|---|---|---|---|---|---|---|
| 1-49 | COOEt | H | H | H | 3-Cl, 4-OMe phenyl | 3-methyl-1H-pyrazole | NMR |
| 1-50 | COOEt | H | H | H | 3-Cl, 4-OMe phenyl | 5-methyloxazole | [195–197] |
| 1-51 | COOEt | H | H | H | 3-Cl, 4-OMe phenyl | 5-methyl-1,3,4-oxadiazole | [100–102] |
| 1-52 | CO₂Me | H | H | H | 3-Cl, 4-OMe phenyl | 1,4-dimethylpyrazole | |
| 1-53 | Me | H | H | H | 3-Cl, 4-OMe phenyl | 3-methylpyridine | [108–111] |
| 1-54 | iPr | H | H | H | 3-Cl, 4-OMe phenyl | CONHCH₂COOMe | [155–157] |
| 1-55 | iPr | H | H | H | 3-Cl, 4-OMe phenyl | CONH-(2-OEt-phenyl) | [90] |
| 1-56 | Me | H | H | H | 3-Br, 4-OMe, 5-OMe phenyl | COOEt | NMR |
| 1-57 | Me | H | H | H | 3-Cl, 4-OMe phenyl | CONH-thiazol-2-yl | [183]dec. |

TABLE 1-continued

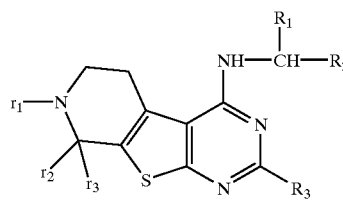

| Compd. No. | r₁ | r₂ | r₃ | R₁ | R₂ | R₃ | Phys. Const. []: m. p. °C. |
|---|---|---|---|---|---|---|---|
| 1-58 | Me | H | H | H | 3-Cl-4-OMe-C₆H₃ | CONH-(4-pyridyl) | [165]dec. |
| 1-59 | Me | H | H | H | 3-Cl-4-OMe-C₆H₃ | CONH-C₆H₄-(4-imidazol-1-yl) | [135]dec. |
| 1-60 | Me | H | H | H | 3-Cl-4-OMe-C₆H₃ | CONH-(2-Cl-C₆H₄) | [145]dec. |
| 1-61 | Me | H | H | H | 3-Cl-4-OMe-C₆H₃ | CONH-(4-Cl-C₆H₄) | [222]dec. |
| 1-62 | Me | H | H | H | 3-Cl-4-OMe-C₆H₃ | CONH-(4-OMe-C₆H₄) | [210]dec. |
| 1-63 | Me | H | H | H | 3-Cl-4-OMe-C₆H₃ | CONH-cyclohexyl | [190]dec. |
| 1-64 | Me | H | H | H | 3-Cl-4-OMe-C₆H₃ | CO-morpholino | [220]dec. |
| 1-65 | CH₂Ph | H | H | H | 3-Cl-4-OMe-C₆H₃ | COOMe | [168–170] |
| 1-66 | CH₂Ph | H | H | H | 3-Cl-4-OMe-C₆H₃ | COOH | [235–238] |
| 1-67 | CH₂Ph | H | H | H | 3-Cl-4-OMe-C₆H₃ | CONH-C₆H₅ | [180]dec. |

TABLE 1-continued

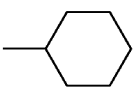

| Compd. No. | $r_1$ | $r_2$ | $r_3$ | $R_1$ | $R_2$ | $R_3$ | Phys. Const. []: m. p. ° C. |
|---|---|---|---|---|---|---|---|
| 1-68 | CH$_2$Ph | H | H | Me | cyclohexyl | COOMe | (S) isomer [160–161] |
| 1-69 | Me | H | H | H | 3-Cl-4-OMe-C$_6$H$_3$ | COOEt | [175–176] |
| 1-70 | CH$_2$Ph | H | H | Me | cyclohexyl | CONHPh | (S) isomer [111–112] |
| 1-71 | Me | H | H | H | 3-Cl-4-OMe-C$_6$H$_3$ | COOH | [270]dec. |
| 1-72 | Me | H | H | H | 3-Cl-4-OMe-C$_6$H$_3$ | CONHPh | [165]dec. |
| 1-73 | iPr | H | H | H | 3-Cl-4-OMe-C$_6$H$_3$ | COOEt | [183] |
| 1-74 | iPr | H | H | H | 3-Cl-4-OMe-C$_6$H$_3$ | COOH | [160]dec. |
| 1-75 | iPr | H | H | H | 3-Cl-4-OMe-C$_6$H$_3$ | CONHPh | [180]dec. |
| 1-76 | iPr | H | H | H | 3-Cl-4-OMe-C$_6$H$_3$ | CONHcPr | [112–114] |
| 1-77 | Me | H | H | H | 3-Cl-4-OMe-C$_6$H$_3$ | CO-N-piperidinyl | [200]dec. |

TABLE 1-continued
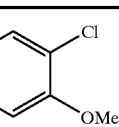
| Compd. No. | r₁ | r₂ | r₃ | R₁ | R₂ | R₃ | Phys. Const. []: m. p. °C. |
|---|---|---|---|---|---|---|---|
| 1-78 | Me | H | H | H | 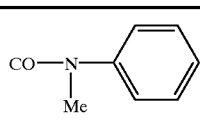 | 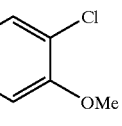 | [181] |
| 1-79 | Me | H | H | H | 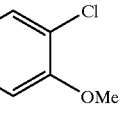 | CONHCH₂Ph | [197]dec. |
| 1-80 | Me | H | H | H | 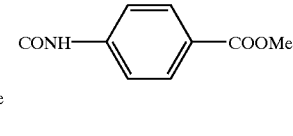 | 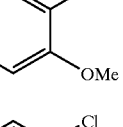 | [175]dec. |
| 1-81 | Me | H | H | H | 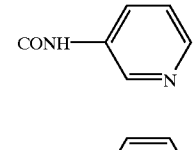 | 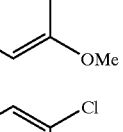 | [145–147] |
| 1-82 | COOEt | H | H | H | 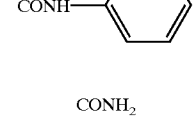 | 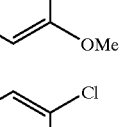 | [190–192] |
| 1-83 | Me | H | H | H | 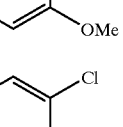 | CONH₂ | [230]dec. |
| 1-84 | COOEt | H | H | H | 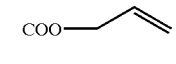 | COOCH₂Ph | [164–166] |
| 1-85 | 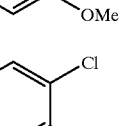 | H | H | H | 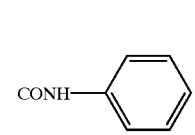 | 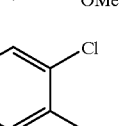 | [165–167] |
| 1-86 | COOMe | H | H | H |  | 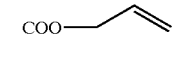 | |
| 1-87 |  | H | H | H | | COOEt | |

TABLE 1-continued
| Compd. No. | r₁ | r₂ | r₃ | R₁ | R₂ | R₃ | Phys. Const. []: m. p. ° C. |
|---|---|---|---|---|---|---|---|
| 1-88 | H | H | H | H | 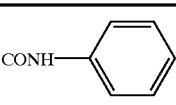 3-Cl, 4-OMe phenyl | CONH-Ph | |
| 1-89 | H | H | H | H |  benzodioxole | CONH-Ph | |
| 1-90 | COPh | H | H | H | 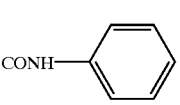 3-Cl, 4-OMe phenyl | CONH-Ph | |
| 1-91 | SO₂Me | H | H | H |  3-Cl, 4-OMe phenyl | CONH-Ph | |
| 1-92 | Me | H | H | H | 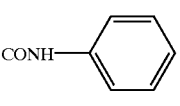 4-pyridyl | CONH-Ph | |
| 1-93 | Me | H | H | H |  3-pyridyl | CONH-Ph | |
| 1-94 | Me | H | H | H | 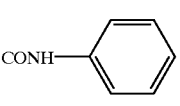 2-Cl-4-pyridyl | CONH-Ph | |
| 1-95 | Me | H | H | H |  2-OMe-4-pyridyl | CONH-Ph | |
| 1-96 | Me | H | H | H | 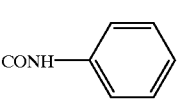 3-Cl, 4-OMe phenyl | CONHNHPh | |
| 1-97 | Me | H | H | H |  3-Cl, 4-OMe phenyl | CONHNHMe | |

TABLE 1-continued

| Compd. No. | r₁ | r₂ | r₃ | R₁ | R₂ | R₃ | Phys. Const. []: m. p. ° C. |
|---|---|---|---|---|---|---|---|
| 1-98 | Me | H | H | H | 3-Cl-4-OMe-phenyl | CONH-(2-furyl) | |
| 1-99 | Me | H | H | H | 3-Cl-4-OMe-phenyl | CONH-(2-thienyl) | |
| 1-100 | Me | H | H | H | 3-Cl-4-OMe-phenyl | CONH-(pyrazinyl) | |
| 1-101 | Me | H | H | H | 3-Cl-4-OMe-phenyl | CONH-(5-oxazolyl) | |
| 1-102 | Me | H | H | H | 3-Cl-4-OMe-phenyl | CONH-(2-oxazolyl) | |
| 1-103 | Me | H | H | H | 3-Cl-4-OMe-phenyl | CONH-(1-Me-2-imidazolyl) | |
| 1-104 | Me | H | H | H | 3-Cl-4-OMe-phenyl | CONH-(benzo[1,3]dioxol-5-yl) | |
| 1-105 | Me | H | H | H | 3-Cl-4-OMe-phenyl | CONH-(3-Cl-4-OMe-phenyl) | |
| 1-106 | Me | H | H | H | 3-Cl-4-OMe-phenyl | CONHCH₂-(benzo[1,3]dioxol-5-yl) | |

TABLE 1-continued

| Compd. No. | r₁ | r₂ | r₃ | R₁ | R₂ | R₃ | Phys. Const. []: m. p. °C. |
|---|---|---|---|---|---|---|---|
| 1-107 | CO-(2-thienyl) | H | H | H | 3-Cl-4-OMe-C₆H₃ | CONH-phenyl | |
| 1-108 | CO-(2-furyl) | H | H | H | 3-Cl-4-OMe-C₆H₃ | CONH-phenyl | |
| 1-109 | CO-(2-pyridyl) | H | H | H | 3-Cl-4-OMe-C₆H₃ | CONH-phenyl | |
| 1-110 | Me | H | H | H | 3-Cl-4-OMe-C₆H₃ | CONHCH₂-(4-pyridyl) | |
| 1-111 | Me | H | H | H | 3-Cl-4-OMe-C₆H₃ | CONHCH₂-(2-furyl) | [200]dec. |
| 1-112 | Me | H | H | H | 3-Cl-4-OMe-C₆H₃ | CONHCH₂-(2-pyrazinyl) | |
| 1-113 | Me | H | H | H | 3-Cl-4-OMe-C₆H₃ | CONHCH₂-(1-imidazolyl) | |
| 1-114 | Me | H | H | H | 3-Cl-4-OMe-C₆H₃ | CONHCH₂-(1-Me-2-imidazolyl) | |
| 1-115 | Me | H | H | H | 3-Cl-4-OMe-C₆H₃ | CONHCH₂-(2-oxazolyl) | |
| 1-116 | Me | H | H | H | 3-Cl-4-OMe-C₆H₃ | CONHCH₂-(2-thiazolyl) | |

TABLE 1-continued

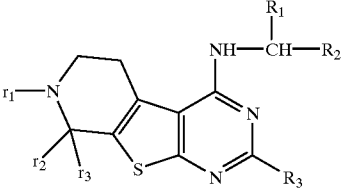

| Compd. No. | r₁ | r₂ | r₃ | R₁ | R₂ | R₃ | Phys. Const. []: m. p. °C. |
|---|---|---|---|---|---|---|---|
| 1-117 | Me | H | H | H | 3-Cl, 4-OMe phenyl | CONH-CH₂CH₂-pyrrolidinyl | [170–173] |
| 1-118 | Me | H | H | H | 3-Cl, 4-OMe phenyl | CONH-CH₂CH₂-N(Ac) | [120–122] |
| 1-119 | Me | H | H | H | 3-Cl, 4-OMe phenyl | CONH-CH₂CH₂-piperazinyl | [163–165] |
| 1-120 | Me | H | H | H | 3-Cl, 4-OMe phenyl | CONH-CH₂CH₂-piperidinyl | [167–169] |
| 1-121 | Me | H | H | H | 3-Cl, 4-OMe phenyl | CONH-CH₂-(1,3-dioxolan-2-yl) | [127–128] |
| 1-122 | COOEt | H | H | H | 3-Cl, 4-OMe phenyl | CONH-thiazol-2-yl | [115–117] |
| 1-123 | COOEt | H | H | H | 3-Cl, 4-OMe phenyl | CONH-pyridin-3-yl | [175–177] |
| 1-124 | COOEt | H | H | H | 3-Cl, 4-OMe phenyl | CONH-pyridin-2-yl | [113–116] |
| 1-125 | COOEt | H | H | H | 3-Cl, 4-OMe phenyl | CONHNH₂ | NMR |
| 1-126 | COOEt | H | H | H | 3-Cl, 4-OMe phenyl | CHO | NMR |

TABLE 1-continued
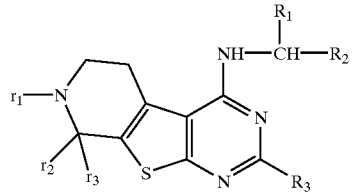
| Compd. No. | $r_1$ | $r_2$ | $r_3$ | $R_1$ | $R_2$ | $R_3$ | Phys. Const. []: m. p. °C. |
|---|---|---|---|---|---|---|---|
| 1-127 | Me | H | H | H | 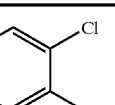 | CONHNHPh | [240]dec. |
| 1-128 | Me | H | H | H | 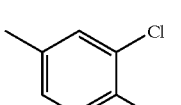 | CONHOPh | [195–197] |
| 1-129 | Me | H | H | H | 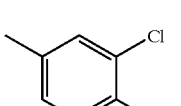 | 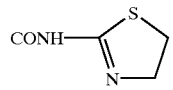 | [120–121] |
| 1-130 | Me | H | H | H | 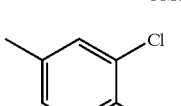 | 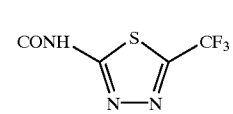 | [141–143] |
| 1-131 | Me | H | H | H | 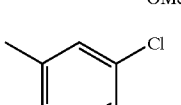 | 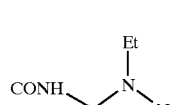 | NMR |
| 1-132 | Me | H | H | H | 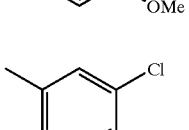 | 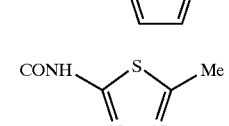 | [178–180] |
| 1-133 | Me | H | H | H | 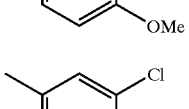 | 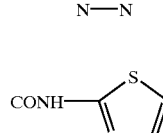 | hydrochloride [183–185] |
| 1-134 | COOEt | H | H | H | 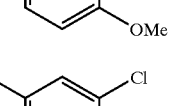 | 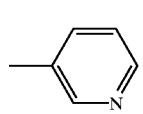 | hydrochloride NMR |
| 1-135 | Me | H | H | H | 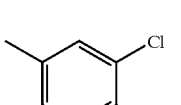 | 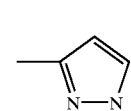 | hydrochloride NMR |
| 1-136 | Me | H | H | H | 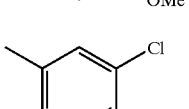 | 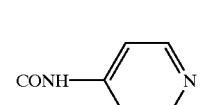 | hydrochloride [223–224] |

TABLE 1-continued

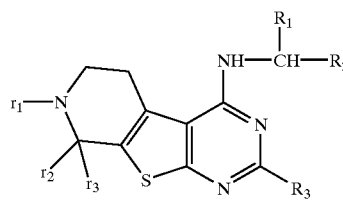

| Compd. No. | r₁ | r₂ | r₃ | R₁ | R₂ | R₃ | Phys. Const. []: m. p. °C. |
|---|---|---|---|---|---|---|---|
| 1-137 | Me | H | H | H | 3-Cl-4-OMe-C₆H₃ | CONH-(4-OMe-C₆H₄) | hydrochloride [176–177] |
| 1-138 | iPr | H | H | H | 3-Cl-4-OMe-C₆H₃ | CONH-Ph | hydrochloride [180–182] |
| 1-139 | COOEt | H | H | H | 3,4-methylenedioxyphenyl | 4-pyridyl | hydrochloride [150–152] |
| 1-140 | Me | H | H | H | 3-Cl-4-OMe-C₆H₃ | CONH-(1-Et-pyrazol-5-yl) | hydrochloride NMR |
| 1-141 | COMe | H | H | H | 3-Cl-4-OMe-C₆H₃ | 3-pyridyl | hydrochloride NMR |
| 1-142 | Me | H | H | H | 3-Cl-4-OMe-C₆H₃ | CONH-Ph | hydrochloride [185–187] |
| 1-143 | H | H | H | H | 3-Cl-4-OMe-C₆H₃ | 3-pyridyl | hydrochloride [228–231] |
| 1-144 | CH₂Ph | H | H | H | 3-Cl-4-OMe-C₆H₃ | CONH-Ph | hydrochloride [168–170] |
| 1-145 | CO₂Et | H | H | H | 3-Cl-4-OMe-C₆H₃ | CONH-(4-pyridyl) | hydrochloride |
| 1-146 | Me | H | H | H | 3-Cl-4-OMe-C₆H₃ | CONH-(2-pyridyl) | |

TABLE 1-continued

| Compd. No. | r₁ | r₂ | r₃ | R₁ | R₂ | R₃ | Phys. Const. []: m. p. °C. |
|---|---|---|---|---|---|---|---|
| 1-147 | Me | H | H | H | 3-Cl-4-OMe-phenyl | CONH-(1,3,5-trimethylpyrazol-4-yl) | [128–130] |
| 1-148 | Me | H | H | H | 3-Cl-4-OMe-phenyl | CONH-(1H-pyrazol-3-yl) | |
| 1-149 | COMe | H | H | H | 3-Cl-4-OMe-phenyl | CONH-phenyl | |
| 1-150 | COMe | H | H | H | 3-Cl-4-OMe-phenyl | CONH-(thiazol-2-yl) | |
| 1-151 | COMe | H | H | H | 3-Cl-4-OMe-phenyl | CONH-(pyridin-4-yl) | |
| 1-152 | COMe | H | H | H | 3-Cl-4-OMe-phenyl | CONH-(pyridin-3-yl) | |
| 1-153 | COMe | H | H | H | 3-Cl-4-OMe-phenyl | CONH-(pyridin-2-yl) | |
| 1-154 | Me | H | H | H | 3-Cl-4-OMe-phenyl | 4-methyl-1H-pyrazol-3-yl | |
| 1-155 | CO₂Et | H | H | H | 3-Cl-4-OMe-phenyl | 4-methyl-1H-pyrazol-3-yl | |

TABLE 1-continued
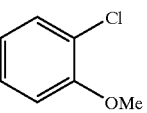
| Compd. No. | $r_1$ | $r_2$ | $r_3$ | $R_1$ | $R_2$ | $R_3$ | Phys. Const. []: m. p. ° C. |
|---|---|---|---|---|---|---|---|
| 1-156 | Me | H | H | H | 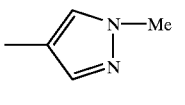 | 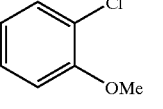 | |
TABLE 2
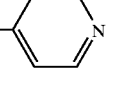
| Compound No. | $r_1$ | $R_1$ | $R_2$ | $R_3$ | Physical costant []: m.p.° C. |
|---|---|---|---|---|---|
| 2-1 | Me | H | 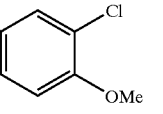 | 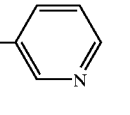 | |
| 2-2 | Me | H | 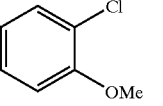 | 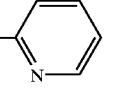 | |
| 2-3 | Me | H | 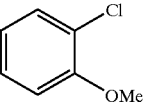 | 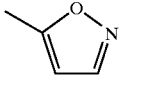 | |
| 2-4 | Me | H | 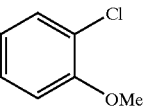 | 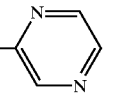 | |
| 2-5 | Me | H | 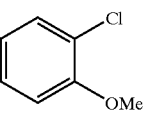 | 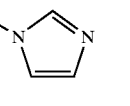 | |
| 2-6 | Me | H |  |  | |

TABLE 2-continued
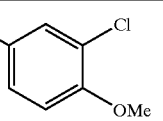
| Compound No. | $r_1$ | $R_1$ | $R_2$ | $R_3$ | Physical costant []: m.p.° C. |
|---|---|---|---|---|---|
| 2-7 | Me | H | 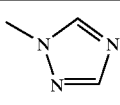 | 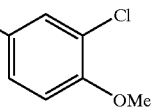 | |
| 2-8 | H | H | 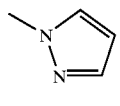 | 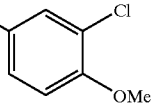 | |
| 2-9 | COMe | H | 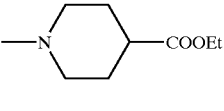 | 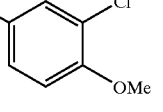 | |
| 2-10 | iPr | H | 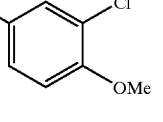 | CH2COOEt | NMR |
| 2-11 | Me | H | 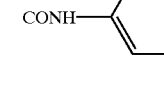 | 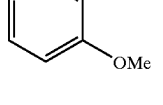 | [128–130] |
| 2-12 | Me | H | 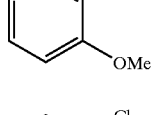 | COOEt | [235–236] |
| 2-13 | Me | H | 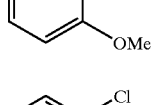 | COOH | [218–220] |
| 2-14 | Me | H | 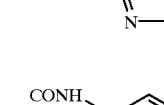 | 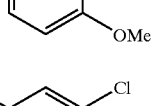 | |
| 2-15 | Me | H | 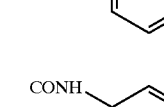 | 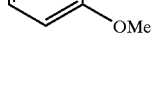 | |
| 2-16 | Me | H | 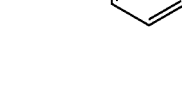 | | |

TABLE 2-continued
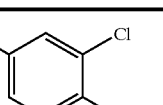
| Compound No. | r₁ | R₁ | R₂ | R₃ | Physical constant []: m.p.° C. |
|---|---|---|---|---|---|
| 2-17 | Me | H | 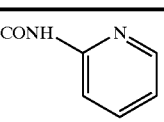 | 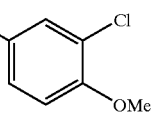 | |
| 2-18 | Me | H | 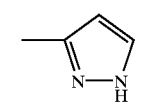 | 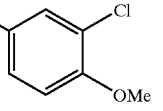 | |
| 2-19 | Me | H | 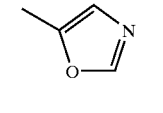 | 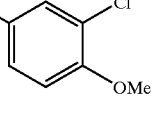 | |
| 2-20 | Me | H | 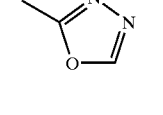 | 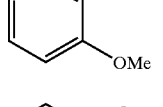 | |
| 2-21 | Me | H | 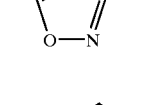 | 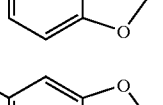 | |
| 2-22 | Me | H | 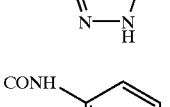 | 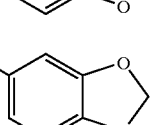 | |
| 2-23 | Me | H | 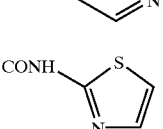 | 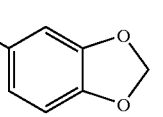 | |
| 2-24 | Me | H | 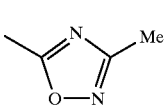 | 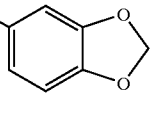 | |
| 2-25 | Me | H | 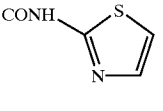 | 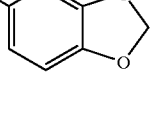 | |
| 2-26 | Me | Me | 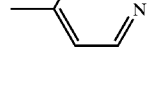 |  | |
| 2-27 | Me | Me |  | | |

TABLE 2-continued

| Compound No. | r₁ | R₁ | R₂ | R₃ | Physical constant []: m.p.° C. |
|---|---|---|---|---|---|
| 2-28 | Me | H | 1,3-benzodioxol-5-yl | 3-pyridyl | |
| 2-29 | Me | H | 1,3-benzodioxol-5-yl | 2-pyridyl | |
| 2-30 | Me | H | 1,3-benzodioxol-5-yl | CONH-phenyl | |
| 2-31 | Et | H | 1,3-benzodioxol-5-yl | CONH-phenyl | |
| 2-32 | Et | H | 3-Cl-4-OMe-phenyl | CONH-phenyl | |
| 2-33 | Et | H | 3-Cl-4-OMe-phenyl | CONH-(2-thiazolyl) | |
| 2-34 | Et | H | 3-Cl-4-OMe-phenyl | 4-pyridyl | |
| 2-35 | Et | H | 3-Cl-4-OMe-phenyl | 3-pyridyl | |
| 2-36 | Et | H | 3-Cl-4-OMe-phenyl | 2-pyridyl | |
| 2-37 | Et | H | 3-Cl-4-OMe-phenyl | CONH-(3-pyridyl) | |
| 2-38 | Me | H | 3-Cl-4-OMe-phenyl | CONH-(3-pyrazolyl) | |

TABLE 3

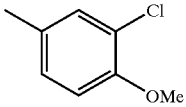

| Compd. No. | Q | R₁ | R₂ | R₃ | Phys. Const. []: m.p.° C. |
|---|---|---|---|---|---|
| 3-1 | (CH₂)₄ | H | 3-Cl-4-OMe-phenyl | COOEt | [151–153] |
| 3-2 | (CH₂)₄ | H | 3-Cl-4-OMe-phenyl | CONH-phenyl | [210–211] |
| 3-3 | (CH₂)₄ | H | 3-Cl-4-OMe-phenyl | CONH-phenyl | [190]dec. |
| 3-4 | CH=CHCH=CH | H | 3-Cl-4-OMe-phenyl | CONH-phenyl | [158–160] |
| 3-5 | (CH₂)₄ | H | 3-Cl-4-OMe-phenyl | CONH-(1H-pyrazol-3-yl) | |
| 3-6 | (CH₂)₄ | H | 3-Cl-4-OMe-phenyl | CONH-(1H-pyrazol-3-yl) | |
| 3-7 | (CH₂)₄ | H | 3-Cl-4-OMe-phenyl | CONH-(thiazol-2-yl) | |
| 3-8 | (CH₂)₃ | H | 3-Cl-4-OMe-phenyl | CONH-(pyridin-4-yl) | |
| 3-9 | (CH₂)₄ | H | 3-Cl-4-OMe-phenyl | CONH-(pyridin-3-yl) | |
| 3-10 | (CH₂)₄ | H | 3-Cl-4-OMe-phenyl | CONH-(pyridin-2-yl) | |

TABLE 3-continued

[Structure: thieno[2,3-d]pyrimidine core with Q fused ring (positions a,b), NH-CH(R1)(R2) at 4-position, R3 at 2-position]

| Compd. No. | Q | R₁ | R₂ | R₃ | Phys. Const. []: m.p.° C. |
|---|---|---|---|---|---|
| 3-11 | (CH₂)₃ | H | 3-Cl-4-OMe-phenyl | CONH-(thiazol-2-yl) | |
| 3-12 | (CH₂)₃ | H | 3-Cl-4-OMe-phenyl | CONH-(pyridin-4-yl) | |
| 3-13 | (CH₂)₃ | H | 3-Cl-4-OMe-phenyl | CONH-(pyridin-3-yl) | |
| 3-14 | (CH₂)₃ | H | 3-Cl-4-OMe-phenyl | CONH-(pyridin-2-yl) | |
| 3-15 | CH=CHCH=CH | H | 3-Cl-4-OMe-phenyl | CONH-(pyridin-4-yl) | Offie |
| 3-16 | CH=CHCH=CH | H | 3-Cl-4-OMe-phenyl | CONH-(pyridin-3-yl) | |
| 3-17 | CH=CHCH=CH | H | 3-Cl-4-OMe-phenyl | CONH-(pyridin-2-yl) | |
| 3-18 | (CH₂)₄ | Me | 3-Cl-4-OMe-phenyl | CONH-(thiazol-2-yl) | |
| 3-19 | (CH₂)₃ | Me | 3-Cl-4-OMe-phenyl | CONH-(thiazol-2-yl) | |
| 3-20 | CH=CHCH=CH | Me | 3-Cl-4-OMe-phenyl | CONH-(thiazol-2-yl) | |

TABLE 3-continued

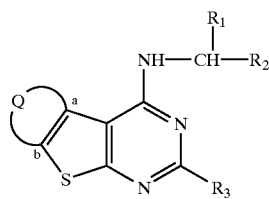

| Compd. No. | Q | R₁ | R₂ | R₃ | Phys. Const. []: m.p.° C. |
|---|---|---|---|---|---|
| 3-21 | (CH₂)₄ | H | benzo[1,3]dioxole | CONH-thiazol-2-yl | |
| 3-22 | (CH₂)₃ | H | benzo[1,3]dioxole | CONH-thiazol-2-yl | |
| 3-23 | CH=CHCH=CH | H | benzo[1,3]dioxole | CONH-thiazol-2-yl | |
| 3-24 | CH=CHCH=CH | H | 2-Cl-4-OMe-phenyl | CONH-thiazol-2-yl | |
| 3-25 | CH=CHCH=CH | H | 2-Cl-4-OMe-phenyl | CONH-pyrazol-3-yl | |
| 3-26 | (CH₂)₄ | H | 2-Cl-4-OMe-phenyl | CH=CHCONHPh | |
| 3-27 | (CH₂)₄ | H | 2-Cl-4-OMe-phenyl | CH₂CH₂CONHPh | |

TABLE 4

NMR Data

| Compound No. | ¹H-NMR (CDCl₃, δ ppm) |
|---|---|
| 1-2 | 8.7 (2H, d), 8.3 (2H, d), 6.8–6.9 (3H, m), 6.0 (2H, s), 5.5 (1H, br), 4.8 (2H, d), 4.7 (2H, brs), 4.2 (2H, q), 3.8 (2H, t), 3.0 (2H, brs), 1.3 (3H, t) |
| 1-42 | 7.65 (1H, s), 7.3 (1H, d), 7.1 (1H, d), 7.1–7.0 (3H, m), 5.6(1H, t), 5.1 (2H, s), 4.5 (2H, d), 3.85 (3H, s), 3.6 (2H, s), 2.95 (2H, brs), 2.75 (2H, t), 2.45 (3H, s) |
| 1-43 | 7.65 (1H, s), 7.35 (1H, d), 7.2 (1H, d), 7.0 (1H, s), 6.85 (1H, d), 5.5 (1H, t), 4.7 (2H, d), 3.85 (3H, s), 3.65 (2H, s), 3.0 (2H, brs), 2.8 (2H, t), 2.5 (3H, s) |
| 1-44 | 8.0 (1H, s), 7.8 (1H, s), 7.4 (1H, s), 7.25 (1H, d), 6.9 (1H, d), 5.55 (1H, t), 4.75 (2H, d), 3.9 (3H, s), 3.65 (2H, s), 3.0 (2H, brs), 2.8 (2H, t), 2.5 (3H, s) |
| 1-49 | 7.65 (1H, s), 7.4 (1H, s), 7.25 (1H, d), 7.0 (1H, s), 6.9 (1H, d), 5.5 (1H, brs), 4.75 (2H, d), 4.7 (2H, s), 4.2 (2H, q), 3.9 (3H, s), 3.8 (2H, t), 2.9 (2H, brs), 1.3 (3H,t) |
| 1-56 | 7.5(1H, t), 7.3 (2H, s), 4.6 (2H, d), 4.3 (2H, q), 3.8 (5H, s), 3.7 (3H, s), 3.1 (2H, brs), 2.9 (2H, brs), 1.3 (3H, t) |
| 1-125 | 8.8 (1H, s), 7.4 (1H, s), 7.2 (1H, d), 6.9 (1H, d), 5.6 (1H, br), 4.7 (4H, m), 4.2–4.3 (4H, m), 3.9 (3H, s), 3.8 (2H, t), 3.0 (2H, brs), 1.3 (3H, t) |

TABLE 4-continued

NMR Data

| Compound No. | $^1$H-NMR (CDCl$_3$, δ ppm) |
|---|---|
| 1-126 | 10.0 (1H, s), 7.4 (1H, s), 7.3 (1H, d), 6.9 (1H, d), 5.6 (1H, br), 4.7–4.8 (4H, m), 4.2 (2H, q), 3.9 (3H, s), 3.8 (2H, t), 3.0 (2H, brs), 1.3 (3H, t) |
| 1-131 | 7.6–7.4 (4H, in), 7.05 (1H, d), 6.25 (1H, s), 4.8 (2H, d), 3.95 (2H, q), 3.8 (3H, s), 3.6 (2H, brs), 3.1 (2H, brs), 2.75 (2H, brs), 2.4 (3H, s), 1.25 (3H, t) |
| 1-134 | 9.6 (1H, s), 9.5 (1H, d), 8.8 (1H, d), 8.0 (1H, t), 7.4 (1H, s), 7.3 (1H, d), 7.0 (1H, d), 6.9 (1H, br), 4.8 (2H, brs), 4.7 (2H, S), 4.2 (2H, q), 3.8 (3H, s), 3.8 (2H, brs), 3.2 (2H, brs), 1.3 (3H, t) |
| 1-135 | 8.0 (1H, br), 7.8 (1H, s), 7.6 (1H, s), 7.5 (1H, d), 7.1 (1H, d), 7.0 (1H, s), 4.8 (2H, br), 4.4 (2H, br), 3.8 (3H, s), 3.7 (2H, br), 3.4 (2H, br), 2.9 (3H, s) |
| 1-140 | 7.9 (1H, br), 7.6 (1H, s), 7.5 (1H, s), 7.4 (1H, d), 7.1 (1H, d), 6.3 (1H s), 4.8 (2H, br), 4.5 (2H, br), 4.0 (2H, q), 3.8 (3H, s), 3.5 (4H, br), 2.9 (3H, s), 1.3 (3H, t) |
| 1-141 | 9.5 (1H, s), 9.2 (1H, d), 9.0 (1H, d), 8.1 (1H, m), 7.7 (1H, m), 7.6 (1H, s), 7.5 (1H, d), 7.1 (1H, d), 4.8 (4H, brs), 3.8 (5H, brs), 3.2 (2H, br), 2.1(3H, s) |
| 2-10 | 7.4 (1H, s), 7.25 (1H, dd), 6.9 (2H, d), 5.4 (1H, t), 4.95 (1H, m), 4.7 (2H, d), 4.2 (2H, q), 3.9 (5H, s), 3.55 (2H, t), 3.05 (2H, t), 1.25 (3H, t), 1.2 (6H, d) |

Industrial Applicability

Pharmacological activities of the compounds of the present invention are described in the following.

Pharmacological Test Example 1: Phosphodiesterase Inhibiting Activity

Cyclic nucleotide phosphodiesterases from human platelets and from the heart and kidney of a dog were eluted by the concentration gradient method with 70 to 1000 mM of sodium acetate on DEAE-cellulose column chromatography (Whatman Co. Ltd., DE-52, φ3.2×13 cm) according to the method of Thompson and others (Thompson W. J., et al., Advances in Cyclic Nucleotide Research: 10, 69–92, 1979), and separated into isozymes. PDE 5 (cGMP specific PDE) and PDE 3 (cGMP inhibitable cAMP PDE) were separated from the platelets, PDE 1 (Ca-calmodulin activatable PDE) from the heart, and PDE 4 (cGMP non-inhibitable cAMP PDE) from the kidney. The method of Thompson, et al was partially modified to measure phosphodiesterase activities: 1 μM of [3H]-cAMP or [3H]-cGMP was decomposed with phosphodiesterase. The produced 5'-AMP or 5'-GMP was decomposed to adenosine or guanosine with a snake venom (Sigma V7000). The reaction solution was added to anion exchange resin (Bio-Rad Co. Ltd., AG1-X8). Non-adsorbed adenosine or guanosine was counted by a liquid scintillation counter. A concentration causing 50% inhibition of the enzyme activity (IC50) was calculated from concentration inhibition curves. The results are shown in Table 5.

TABLE 5

| Compound | Inhibition of PDE Activity: IC50 (nM) | | | | |
|---|---|---|---|---|---|
| No | PDE 1 | PDE 2 | PDE 3 | PDE 4 | PDE 5 |
| 1-1 | >10000 | 3900 | >10000 | >10000 | 0.92 |
| 1-4 | >10000 | 2700 | 6100 | 2000 | 2.6 |
| 1-5 | >10000 | >10000 | >10000 | 2500 | 0.54 |
| 1-6 | 5500 | >10000 | >10000 | 3600 | 50 |
| 1-7 | >10000 | 2000 | 5400 | 3700 | 2.4 |
| 1-54 | >10000 | >10000 | 10000 | >10000 | 33 |
| 1-55 | >10000 | >10000 | >10000 | 2000 | 62 |
| 1-57 | >10000 | >10000 | >10000 | >10000 | 0.55 |
| 1-58 | >10000 | >10000 | >10000 | >10000 | 2.1 |
| 1-59 | >10000 | 6100 | 7600 | 3400 | 78 |
| 1-60 | >10000 | >10000 | >10000 | 3600 | 14 |
| 1-61 | >10000 | >10000 | >10000 | >10000 | 0.92 |
| 1-62 | >10000 | >10000 | >10000 | >10000 | 2.4 |
| 1-63 | >10000 | >10000 | >10000 | >10000 | 0.38 |
| 1-65 | >10000 | >10000 | >10000 | >10000 | 91 |
| 1-67 | >10000 | >10000 | >10000 | >10000 | 0.39 |
| 1-69 | >10000 | >10000 | >10000 | >10000 | 31 |
| 1-72 | >10000 | >10000 | >10000 | >10000 | 1.8 |
| 1-75 | >10000 | >10000 | >10000 | 8400 | 1.4 |
| 1-76 | >10000 | >10000 | >10000 | >10000 | 56 |
| 1-79 | 670 | >10000 | >10000 | 5100 | 16 |
| 1-80 | >10000 | 3300 | >10000 | 4100 | 53 |
| 1-81 | >10000 | >10000 | >10000 | 6400 | 6.0 |
| 1-83 | 1300 | 3100 | >10000 | >10000 | 75 |
| 2-10 | >10000 | >10000 | 7400 | 8000 | 39 |
| 3-2 | >10000 | >10000 | >10000 | >10000 | 0.39 |
| Control | 2000 | 30000 | 53000 | >10000 | 14 |

Control: Sildenafil

Pharmacological Test Example 2: Vasodilating Activity

A vasodilating activity was assessed according to the method of Ken-ichi Hirata and Mitsuhiro Yokoyama (Arteriosclerosis and Hyperlipemia Research Strategies, published by Shujunsha (Japan), pages 275–277, 1996): The thoracic aortas were extracted from Sprague-Dawley male rats (weighing 180 to 360 g). After unnecessary connective tissues were removed, the aortas were cut to 5mm-long pieces to make ring strip preparations, and assessed by the Magnus method (37° C.). A nutrient solution used was a Krebs-Henseleit solution aerated with 5% carbon dioxide gas and 95% oxygen gas. Specimens were equilibrated for about 60 minutes, and then contracted by adding 1 μM of phenylephrine. 1 μM of acetylcholine was added at the second phenylepherine-induced contraction in order to confirm an endothelial cell dependent relaxation response. At the third phenylepherine-induced contraction, a drug to test was added cumulatively, and the relaxation action was observed. Drugs to test were all dissolved in DMSO to use for the tests. The tested drugs were assessed by 50% relaxation rates (EC50) obtained from vasodilation rates to respective concentrations (the maximum relaxation was measured by adding 100 μM of papaverine). The results are shown in Table 6.

TABLE 6

| Compound No. | Vasodilating Activity EC50 (nM) | Compound No. | Vasodilating Activity EC50 (nM) |
|---|---|---|---|
| 1-1 | 86 | 1-62 | 7.2 |
| 1-4 | 19 | 1-63 | 4.8 |
| 1-5 | 8.1 | 1-65 | 260 |
| 1-6 | 16 | 1-67 | 82 |
| 1-7 | 9.5 | 1-69 | 18 |
| 1-9 | 6.3 | 1-72 | 7.4 |
| 1-15 | 2.1 | 1-75 | 9.3 |
| 1-54 | 19 | 1-76 | 26 |
| 1-55 | 180 | 1-79 | 18 |
| 1-57 | 2.7 | 1-80 | 25 |
| 1-58 | 5.1 | 1-81 | 3.1 |
| 1-59 | 7.6 | 2-10 | 18 |
| 1-60 | 7.5 | Control | 6.1 |
| 1-61 | 8.7 | | |

Control: Sildenafil

As described above, the compounds of the present invention have powerful inhibiting activities, highly selective cGMP phosphodiesterase inhibiting activities and vasodilating activities, and are useful for the prevention and/or therapy of, for example, hypertension, heart failure, cardiac infarction, angina pectoris, arteriosclerosis, restenosis after PTCA (percutaneous transluminal coronary angioplasty), cardiac edema, pulmonary hypertension, renal failure, renal edema, hepatic edema, asthma, bronchitis, dementia, immunodeficiency, glaucoma or impotentia.

What is claimed is:

1. A compound represented by Formula (1)

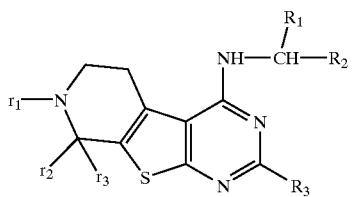

(1)

wherein $r_1$ is hydrogen, $C_{1-6}$ alkyl, $C_{1-6}$ alkylsulfonyl, benzyl optionally substituted with $G_1$, or a group represented by Formula $C(=O)r_4$ or $C(=O)Or_5$;

$r_2$ and $r_3$ are, each independently, hydrogen, $C_{1-6}$ alkyl, phenyl optionally substituted with $G_1$, or $r_2$ and $r_3$ join together to form oxo;

$r_4$ is hydrogen, $C_{1-6}$ alkyl, $C_{2-6}$ alkenyl, phenyl optionally substituted with $G_1$, or a heterocyclic group selected from furyl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl optionally substituted with $G_3$;

$r_5$ is hydrogen, $C_{1-6}$ alkyl, $C_{2-6}$ alkenyl or phenyl optionally substituted with $G_1$;

$R_1$ is hydrogen or $C_{1-6}$ alkyl;

$R_2$ is $C_{3-8}$ cycloalkyl optionally substituted with $G_1$, phenyl optionally substituted with $G_2$ or a heterocyclic group selected from furyl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl optionally substituted with $G_3$;

$R_3$ is a heterocyclic group selected from fliryl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl optionally substituted with G3, or a group represented by Formula $(CH_2)_kC(=O)R_4$ or $CH=CHC(O)R_4$;

$R_4$ is hydroxy, $C_{1-6}$ alkoxy, phenoxy optionally substituted with $G_2$, benzyloxy optionally substituted with $G_2$, or a group represented by Formula $Nr_6r_7$ or $NHNr_8r_9$;

$r_6$ and $r_8$ are hydrogen or $C_{1-6}$ alkyl;

$r_7$ and $r_9$ are hydrogen, $C_{3-8}$ cycloalkyl, $C_{1-6}$ alkyl optionally substituted with a heterocyclic group selected form firyl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl which is optionally substituted with $C_{1-6}$ alkoxycarbonyl or $G_3$, phenyl optionally substituted with $G_1$, benzyl optionally substituted with $G_1$, or a heterocyclic group selected from furyl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl and optionally substituted with $G_3$;

$r_6$ and $r_7$ may join, together with N, to form a ring

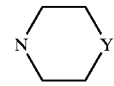

wherein Y is O, $CH_2$ or $Nr_{10}$;

$r_{10}$ is hydrogen, $C_{1-6}$ alkyl, phenyl optionally substituted with $G_1$ or benzyl optionally substituted with $G_1$;

k is 0, 1 or 2;

$G_1$ is halogen, $C_{1-6}$ alkyl or $C_{1-6}$ alkoxy;

$G_2$ is halogen, $C_{1-6}$ alkyl, $C_{1-6}$ alkoxy or $C_{1-2}$ alkylenedioxy;

$G_3$ is halogen, $C_{1-6}$ alkyl, $C_{1-6}$ haloalkyl, $C_{1-6}$ alkoxy or $C_{1-6}$ alkoxycarbonyl; and substituents $G_1$, $G_2$ and $G_3$ on the benzene ring, cycloalkyl or heterocyclic ring may have two or more substituents which may be the same or different.

2. A compound represented by Formula (1-2)

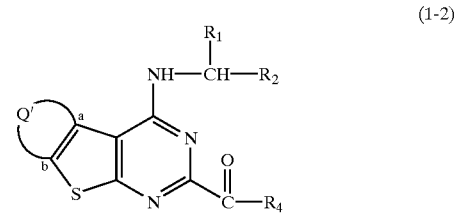

(1-2)

wherein,

Q' is a group bound from a to b and represented by Formula CH=CH—CH=CH or $(CH_2)m$, m is 3, 4 or 5;

$R_1$ is hydrogen or $C_{1-6}$ alkyl;

$R_2$ is $C_{3-8}$ cycloalkyl optionally substituted with $G_1$, phenyl optionally substituted with $G_2$ or a heterocyclic group selected from thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl optionally substituted with $G_3$;

$R_4$ is hydroxy, $C_{1-6}$ alkoxy, phenoxy optionally substituted with $G_2$, benzyloxy optionally substituted with $G_2$, or a group represented by Formula $Nr_6r_7$ or $NHNr_8r_9$;

$r_6$ and $r_8$ are hydrogen or $C_{1-6}$ alkyl;

$r_7$ and $r_9$ are hydrogen, $C_{3-8}$ cycloalkyl, $C_{1-6}$ alkyl optionally substituted with a heterocyclic group selected form furyl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl which is optionally substituted with $C_{1-6}$ alkoxycarbonyl or $G_3$, phenyl optionally substituted with $G_1$, benzyl optionally substituted with $G_1$, or a heterocyclic group selected from furyl, thienyl, pyrrolyl, imidazolyl, pyrazolyl, oxazolyl, isoxazolyl, thiazolyl, isothiazolyl, imidazolyl, triazolyl, oxadiazolyl, pyridyl, pyrimidyl or pyridazinyl and optionally substituted with $G_3$;

$r_6$ and $r_7$ may join, together with N, to form a ring

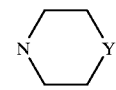

wherein Y is O, $CH_2$ or $Nr_{10}$;

$r_{10}$ is hydrogen, $C_{1-6}$ alkyl, phenyl optionally substituted with $G_1$ or benzyl optionally substituted with $G_1$;

$G_1$ is halogen, $C_{1-6}$ alkyl or $C_{1-6}$ alkoxy;

$G_2$ is halogen, $C_{1-6}$ alkyl, $C_{1-6}$ alkoxy or $C_{1-2}$ alkylenedioxy;

$G_3$ is halogen, $C_{1-6}$ alkyl, $C_{1-6}$ haloalkyl, $C_{1-6}$ alkoxy or $C_{1-6}$ alkoxycarbonyl; and substituents $G_1$, $G_2$ and $G_3$ on the benzene ring, cycloalkyl or heterocyclic ring may have two or more substituents which may be the same or different.

\* \* \* \* \*

UNITED STATES PATENT AND TRADEMARK OFFICE
CERTIFICATE OF CORRECTION

PATENT NO. : 6,482,948 B1
DATED : November 19, 2002
INVENTOR(S) : Hirokazu Yamada et al.

It is certified that error appears in the above-identified patent and that said Letters Patent is hereby corrected as shown below:

Columns 19 and 20,
Table 1, Compd. No. 1-1, $R_3$ column, delete:

" 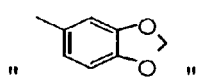 "   and insert:   -- 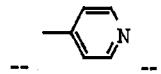 --

Columns 27 and 28,
Table 1, Compd. No. 1-39, $R_3$ column, delete:

" 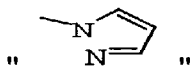 "   and insert:   -- 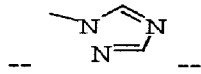 --

Columns 59 and 60,
Table 3, Compd. No. 3-5, delete formula "$(CH_2)_4$" and insert -- $(CH_2)_3$ --
Table 3, Compd. No. 3-8, delete formula "$(CH_2)_3$" and insert -- $(CH_2)_4$ --

Columns 61 and 62,
Table 3, Compd. No. 3-15, remove "Offie"

Signed and Sealed this

Twenty-fifth Day of March, 2003

JAMES E. ROGAN
*Director of the United States Patent and Trademark Office*